United States Patent
Senju

(10) Patent No.: US 10,034,900 B2
(45) Date of Patent: Jul. 31, 2018

(54) METHOD OF PRODUCING MYELOID BLOOD CELLS

(75) Inventor: Satoru Senju, Kumamoto (JP)

(73) Assignee: NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 0 days.

(21) Appl. No.: 13/825,883

(22) PCT Filed: Sep. 28, 2011

(86) PCT No.: PCT/JP2011/072234
§ 371 (c)(1),
(2), (4) Date: Mar. 25, 2013

(87) PCT Pub. No.: WO2012/043651
PCT Pub. Date: Apr. 5, 2012

(65) Prior Publication Data
US 2013/0195818 A1    Aug. 1, 2013

(30) Foreign Application Priority Data

Sep. 30, 2010  (JP) ................. 2010-221809

(51) Int. Cl.
| | | |
|---|---|---|
| *A61K 35/14* | (2015.01) | |
| *C12N 15/85* | (2006.01) | |
| *A61K 35/15* | (2015.01) | |
| *C12N 5/0784* | (2010.01) | |
| *C12N 5/0786* | (2010.01) | |

(52) U.S. Cl.
CPC ............ *A61K 35/15* (2013.01); *C12N 5/0639* (2013.01); *C12N 5/0645* (2013.01); *C12N 15/85* (2013.01); *C12N 2501/22* (2013.01); *C12N 2501/2304* (2013.01); *C12N 2501/60* (2013.01); *C12N 2501/606* (2013.01); *C12N 2502/1394* (2013.01); *C12N 2506/45* (2013.01); *C12N 2510/00* (2013.01)

(58) Field of Classification Search
CPC .... C12N 5/0639; C12N 15/85; C12N 5/0645; C12N 5/0622; C12N 5/063; C12N 2501/22; C12N 2501/2304; C12N 2501/60; C12N 2501/606; C12N 2502/1394; C12N 2506/45; C12N 2510/00; A61K 35/15; A61K 35/30
USPC ...................................... 424/93.21
See application file for complete search history.

(56) References Cited

U.S. PATENT DOCUMENTS

| | | |
|---|---|---|
| 6,627,200 B1 | 9/2003 | Schwarz et al. |
| 2006/0228342 A1 | 10/2006 | Ramirez-Pineda et al. |
| 2007/0116691 A1 | 5/2007 | Cambier et al. |
| 2010/0047217 A1 | 2/2010 | Rafaeli et al. |
| 2012/0122214 A1 | 5/2012 | Senju |

FOREIGN PATENT DOCUMENTS

| | | | |
|---|---|---|---|
| JP | 2003-521439 | 7/2003 | |
| JP | 2005-528899 | 9/2005 | |
| JP | 2007-507206 | 3/2007 | |
| WO | 2005/030939 | 4/2005 | |
| WO | 2007/047583 | 4/2007 | |
| WO | 2008/056734 | 5/2008 | |
| WO | 2010/011644 | 1/2010 | |
| WO | WO-2011003988 A1 * | 1/2011 | ........... C12N 5/0635 |
| WO | 2011/034073 | 3/2011 | |

OTHER PUBLICATIONS

Luo et al., 2005, Blood 106: 2452-2461.*
Baena et al Jul. 2007, Exp. Hematol. 35:1-333-1343.*
Guo et al Feb. 2007, Mol. Biol. Cell 18:536-546.*
Rizo et al.,2009; Blood 114:1468-1505.*
Schuringa 2010, Curr. Opin. Hematol. 17:294-299.*
MoulderTidow et al 2004, Lekemia 18:720-725.*
Hoffman et al 2002, Oncogene 21:3414-3421.*
Senju et al., "Genetically manipulated human embryonic stem cell-derived dendritic cells with immune regulatory function ", Stem Cells, vol. 25, 2007, pp. 2720-2729.
Senju, "Jujo Saibo Ryoho to Tanosei Kansaibo", Dojin News, No. 133, Jan. 2010, pp. 1-5.
Takayama et al., "c-MYC Sai Kasseika ni Tomonau Hito iPS Saibo kara no Koritsu no Yoi Kyokakukyu/Kesshoban Sanseiho no Kakuritsu", Dai 71 Kai The Japanese Society of Hematology Gakujutsu Shukai Program • Shorokushu, 2009, p. 914.
Oguro et al., "'Mijika na Wadai • Sekai no Wadai' (33) Zoketsu Kansaibo no Jiko Fukusei ni Okeru Polycomb Idenshi Bmi-1 no Kino", Hematology Frontier, vol. 16, No. 4, 2006, pp. 608-612.
Bracken et al., "EZH2 is downstream of the pRB-E2F pathway, essential for proliferation and amplified in cancer ", EMBO J., vol. 22, No. 20, 2003, pp. 5323-5335.
Goetz et al., "Requirement for Mdm2 in the Survival Effects of Bcr-Abl and Interleukin 3 in Hematopoietic Cells", Cancer Res., vol. 61, No. 20, 2001, pp. 7635-7641.
Choi et al., "Generation of mature human myelomonocytic cells through expansion and differentiation of pluripotent stem cell-derived lin-CD34+CD43+CD45+ progenitors", J. Clin. Invest., vol. 119, No. 9, 2009, pp. 2818-2829.
Senju, "Anti-Cancer Therapy with Pluripotent Stem Cell-Derived Dendritic Cells ", Biotherapy (Tokyo), vol. 24, No. 2, Mar. 2010, pp. 87-94.
Fairchild et al., "Directed differentiation of dendritic cells from mouse embryonic stem cells", Curr Biol., vol. 10, 2000, pp. 1515-1518.

(Continued)

*Primary Examiner* — Scott Long
*Assistant Examiner* — Kelaginamane Hiriyanna
(74) *Attorney, Agent, or Firm* — Greenblum & Bernstein, P.L.C.

(57) ABSTRACT

An object of the present invention is to provide a method of producing a myeloid blood cell possessing a proliferative capability. According to the present invention, provided is a method of producing a myeloid blood cell possessing a proliferative capability, including forcedly expressing (A) a cMYC gene, and (B) at least one gene selected from the group consisting of a BMI1 gene, an EZH2 gene, an MDM2 gene, an MDM4 gene, and an HIF1A gene in a myeloid blood cell.

5 Claims, 16 Drawing Sheets

(56) References Cited

OTHER PUBLICATIONS

Lindmark et al., "Gene expression profiling shows that macrophages derived from mouse embryonic stem cells is an improved in vitro model for studies of vascular disease", Exp. Cell Res., vol. 300, 2004, pp. 335-344.
Zhan et al., "Functional antigen-presenting leucoytes derived from human embryonic stem cells in vitro", Lancet, vol. 364, 2004, pp. 163-171.
Slukvin et al., "Directed differentiation of human embryonic stem cells into functional dendritic cells through myeloid pathway", J. Immunol., vol. 176, 2006, pp. 2924-2932.
Odegaard et al., "Quantitative expansion of ES cell-derived myeloid progenitors capable of differentiating into macrophages", J. Leukoc. Biol., vol. 81, 2007, pp. 711-719.
Su et al., "Differentiation of human embryonic stem cells into immunostimulatory dendritic cells under feeder-free culture conditions", Clin Cancer Res., vol. 14, 2008, pp. 6207-6217.
Tseng et al., "Generation of immunogenic dendritic cells from human embryonic stem cells without serum and feeder cells", Regen. Med., vol. 4, 2009, pp. 513-526.
International Search Report for PCT/JP2011/072234, dated Jan. 10, 2012, along with an English language translation.
International Preliminary Report on Patentability for PCT/JP2011/072234, dated Apr. 11, 2013, along with an English language translation.
Office Action issued in Japanese Patent Appl. No. 2012-536516, dated Sep. 29, 2015.

* cited by examiner

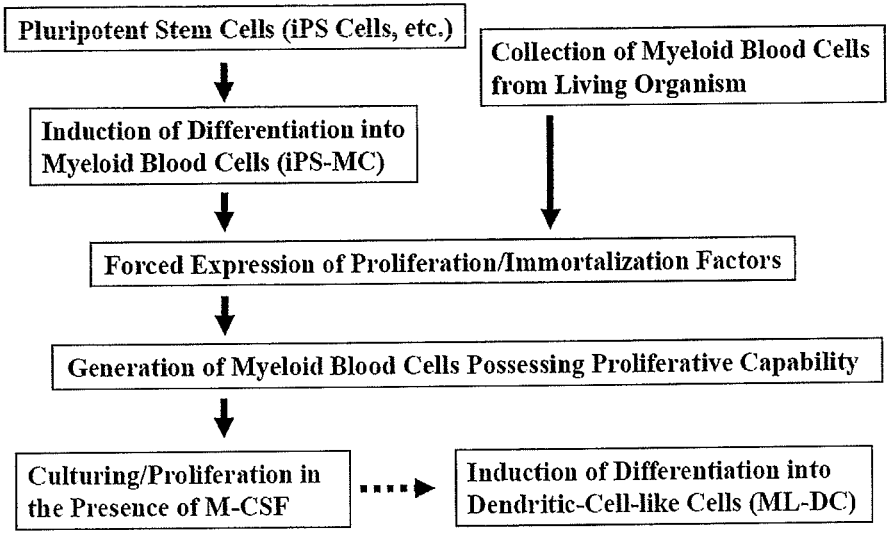
FIG. 1 OUTELINE OF METHOD OF PRODUCING MYELOID BLOOD CELLS POSSESSING PROLIFERATIVE CAPABILITY
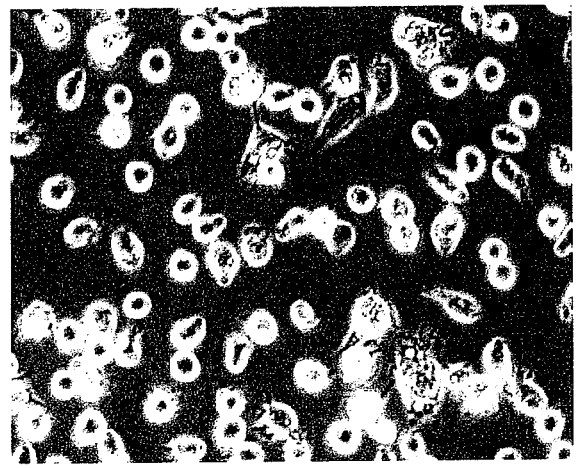
FIG. 2 MORPHOLOGY OF HUMAN iPS CELL–DERIVED MYELOID BLOOD CELL

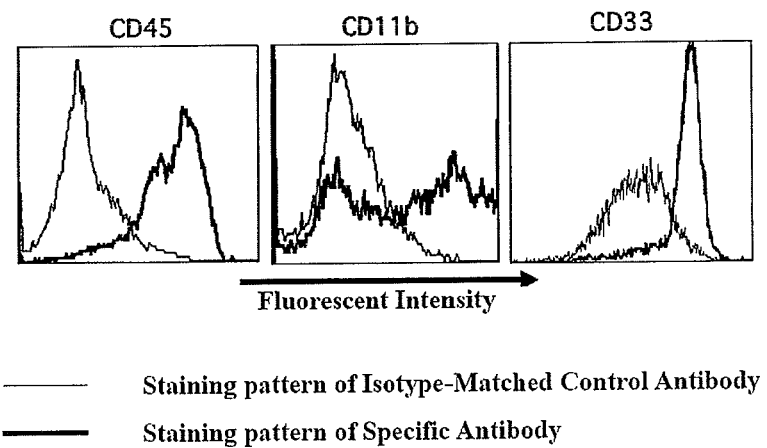
— Staining pattern of Isotype-Matched Control Antibody
— Staining pattern of Specific Antibody
FIG. 3 CELL-SURFACE MOLECULE OF HUMAN iPS CELL-DERIVED MYELOID BLOOD CELL
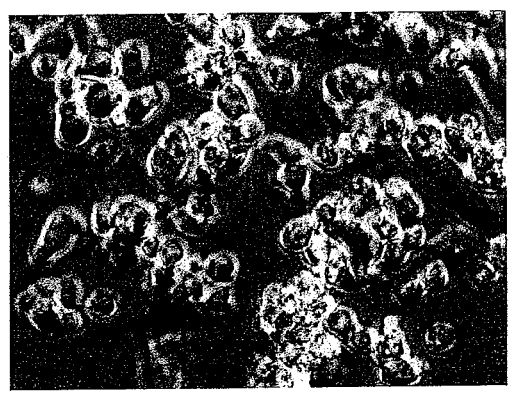
FIG. 4 MORPHOLOGY OF HUMAN iPS CELL-DERIVED MYELOID BLOOD CELL LINE (iPS-ML) GENERATED BY FORCED EXPRESSION OF cMYC AND BMI1

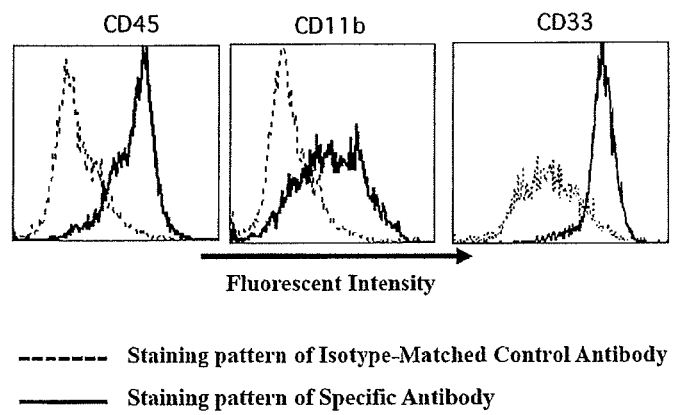
FIG. 5 CELL-SURFACE MOLECULE OF MYELOID BLOOD CELL LINE (iPS-ML) GENERATED BY FORCED EXPRESSION OF cMYC AND BMI1
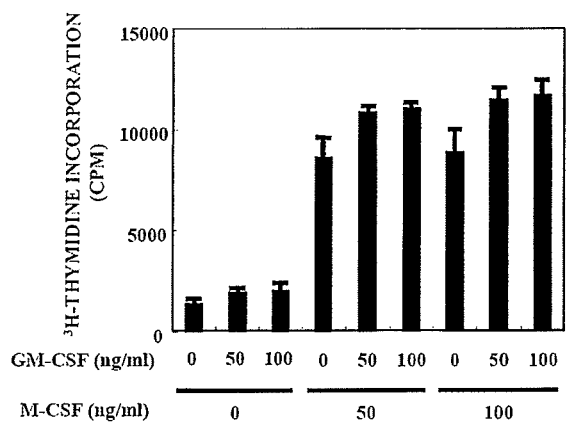
FIG. 6 DEPENDENCE OF PROLIFERATION OF iPS-ML GENERATED BY FORCED EXPRESSION OF cMYC AND BMI1 ON M-CSF AND GM-CSF

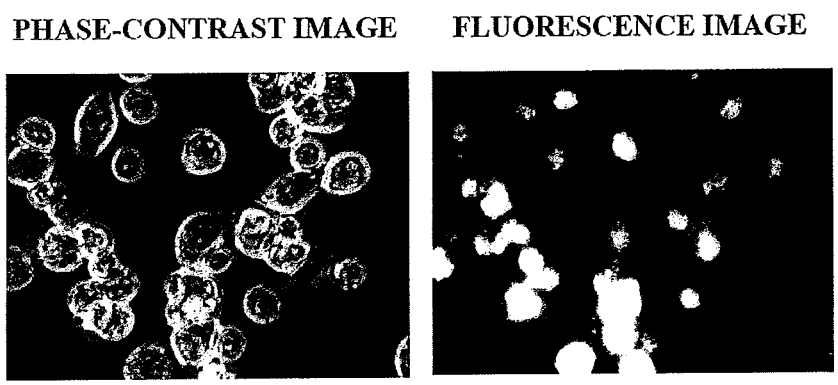
FIG. 7 PHAGOCYTOSIS OF FLUORESCENTLY-LABELED ZYMOSAN
PARTICLE BY iPS-ML
(OBSERVATION WITH FLUORESCENCE MICROSCOPE)
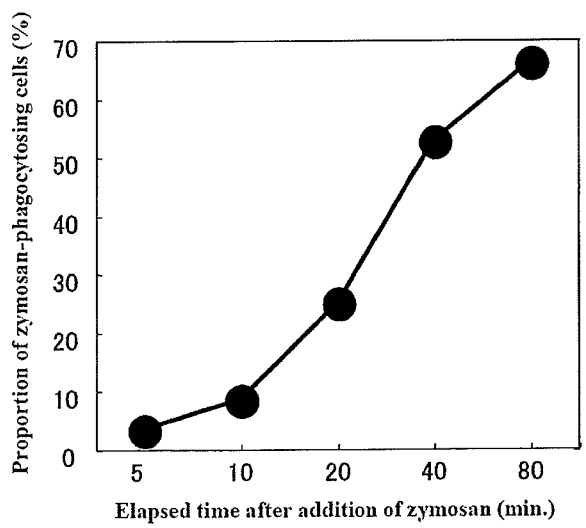
FIG. 8 PHAGOCYTOSIS OF FLUORESCENTLY-LABELED ZYMOSAN
PARTICLE BY iPS-ML (QUANTITATIVE ANALYASIS OF CHANGE
OVER TIME WITH FLOW CYTOMETER)

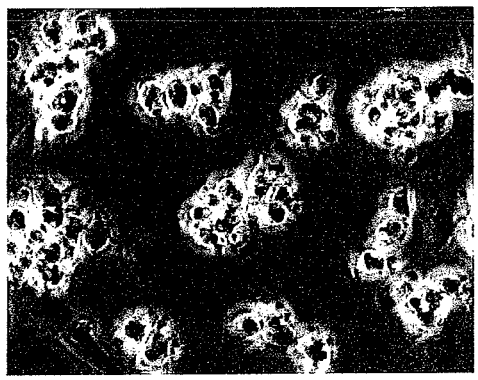
FIG. 9 MORPHOLOGY OF iPS-ML-DERIVED
DENDRITIC-CELL-LIKE CELL (ML-DC)
GENERATED BY FORCED EXPRESSION OF cMYC AND BMI1
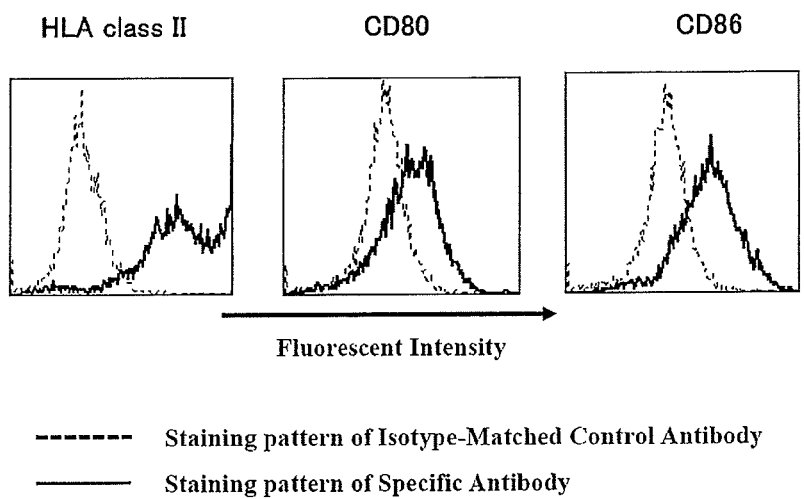
------- Staining pattern of Isotype-Matched Control Antibody
———— Staining pattern of Specific Antibody
FIG. 10 CELL-SURFACE MOLECULE OF iPS-ML-DERIVED
DENDRITIC-CELL-LIKE CELL (ML-DC)
GENERATED BY FORCED EXPRESSION OF cMYC AND BMI1

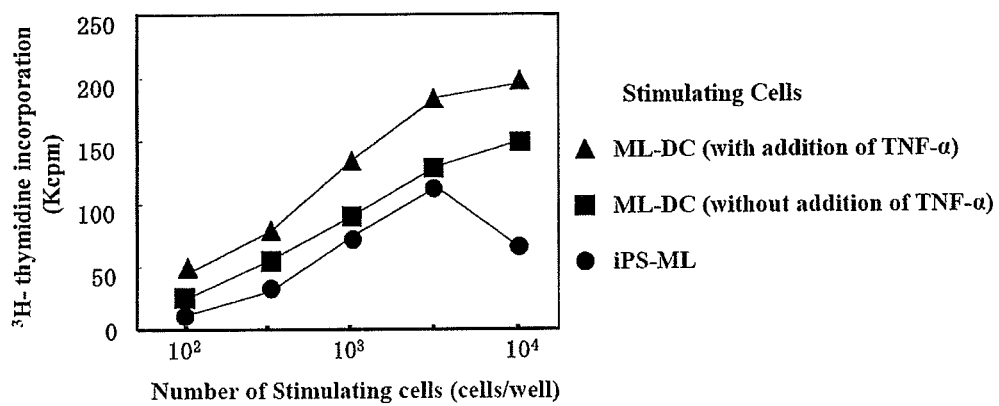
FIG. 11 INDUCTION OF PROLIFERATION REACTION OF ALLO-T CELL BY ML-DC
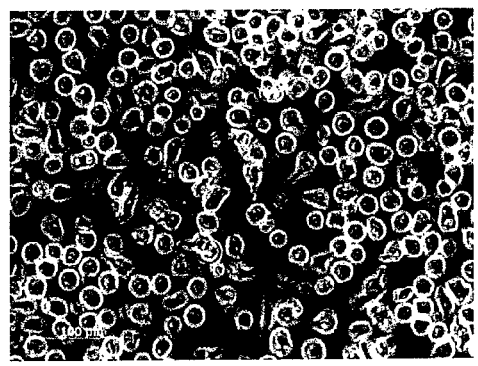
FIG. 12 MORPHOLOGY OF HUMAN iPS CELL-DERIVED MYELOID BLOOD CELL LINE (iPS-ML) GENERATED BY FORCED EXPRESSION OF cMYC AND EZH2

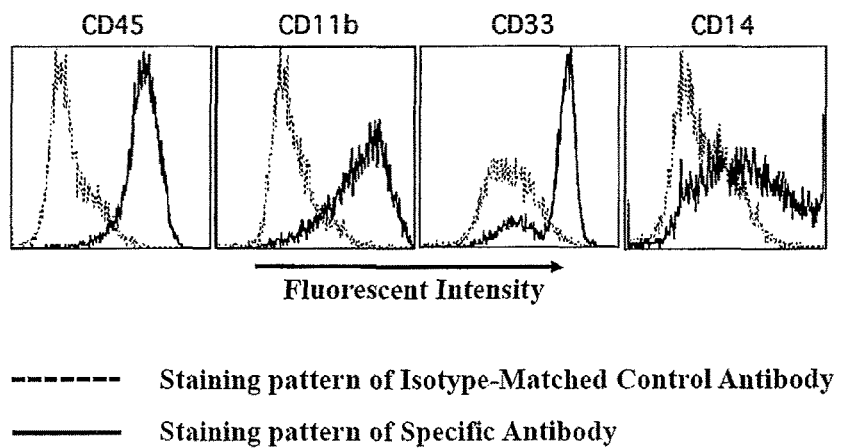
FIG. 13 CELL-SURFACE MOLECULE OF iPS-ML
BY FORCED EXPRESSION OF cMYC AND EZH2
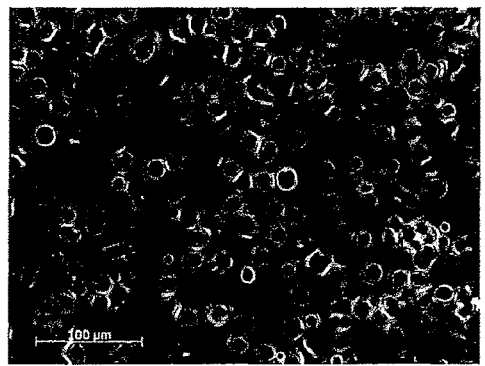
FIG. 14 MORPHOLOGY OF HUMAN iPS CELL-DERIVED
MYELOID BLOOD CELL LINE (iPS-ML)
GENERATED BY FORCED EXPRESSION OF cMYC AND MDM2

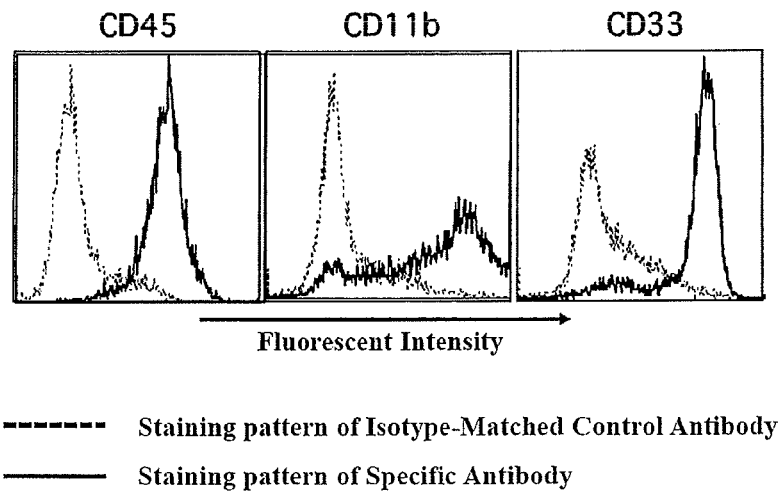
-------- Staining pattern of Isotype-Matched Control Antibody
———— Staining pattern of Specific Antibody
FIG. 15 CELL-SURFACE MOLECULE OF iPS-ML
BY FORCED EXPRESSION OF cMYC AND MDM2
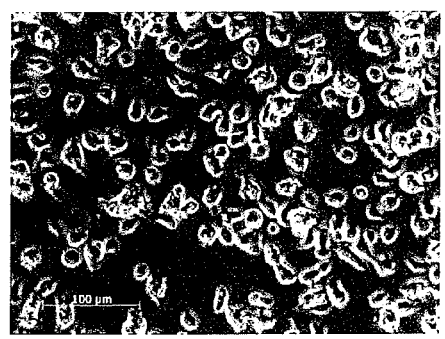
FIG. 16 MORPHOLOGY OF HUMAN iPS CELL-DERIVED
MYELOID BLOOD CELL LINE (iPS-ML)
GENERATED BY FORCED EXPRESSION OF cMYC AND MDM4

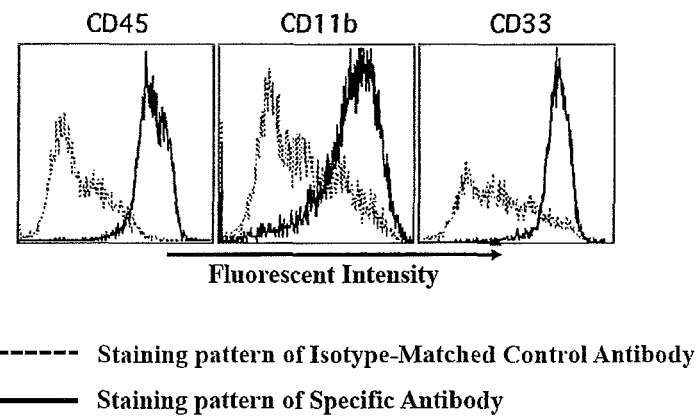
FIG. 17 CELL-SURFACE MOLECULE OF iPS-ML
GENERATED BY FORCED EXPRESSION OF cMYC AND MDM4
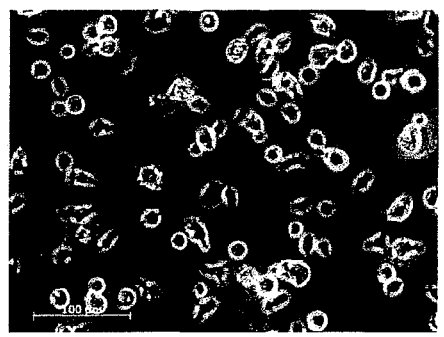
FIG. 18 MORPHOLOGY OF HUMAN iPS CELL-DERIVED
MYELOID BLOOD CELL LINE (iPS-ML)
GENERATED BY FORCED EXPRESSION OF cMYC AND HIF1a

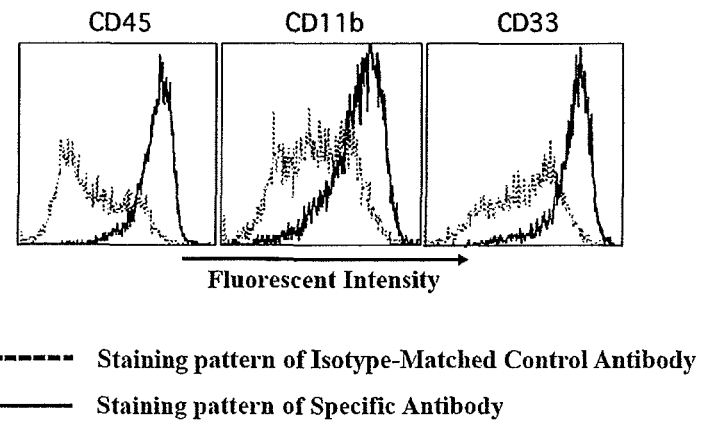
FIG. 19 CELL-SURFACE MOLECULE OF iPS-ML
GENERATED BY FORCED EXPRESSION OF cMYC AND HIF1a
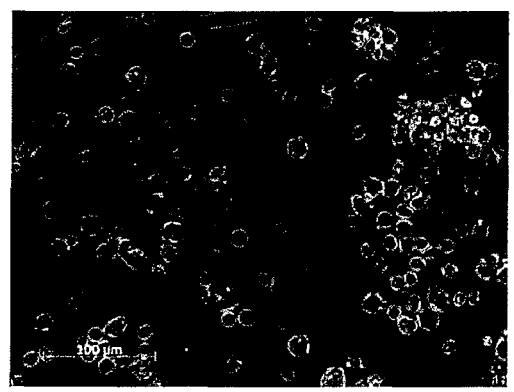
FIG. 20 MORPHOLOGY OF HUMAN iPS CELL-DERIVED
MYELOID BLOOD CELL (WITHOUT USE OF FEEDER CELL)

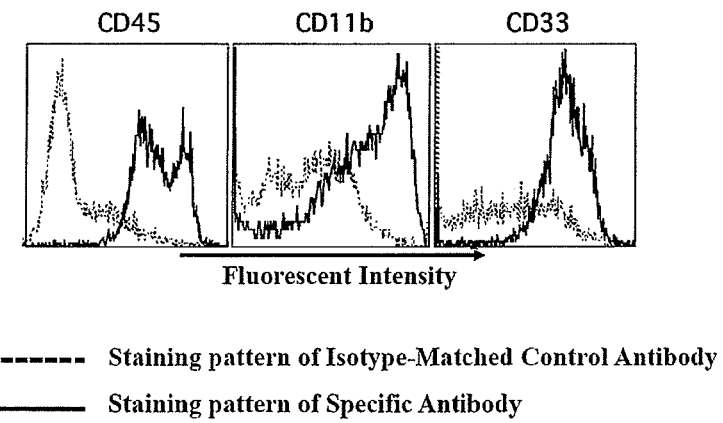
FIG. 21 CELL-SURFACE MOLECULE OF HUMAN iPS-CELL DERIVED MYELOID BLOOD CELL (WITHOUT USE OF FEEDER CELL)
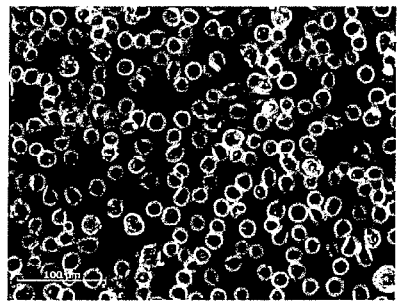
FIG. 22 MORPHOLOGY OF HUMAN iPS CELL-DERIVED
MYELOID BLOOD CELL LINE (iPS-ML)
GENERATED BY FORCED EXPRESSION OF cMYC AND BMI1
(WITHOUT USE OF FEEDER CELL)

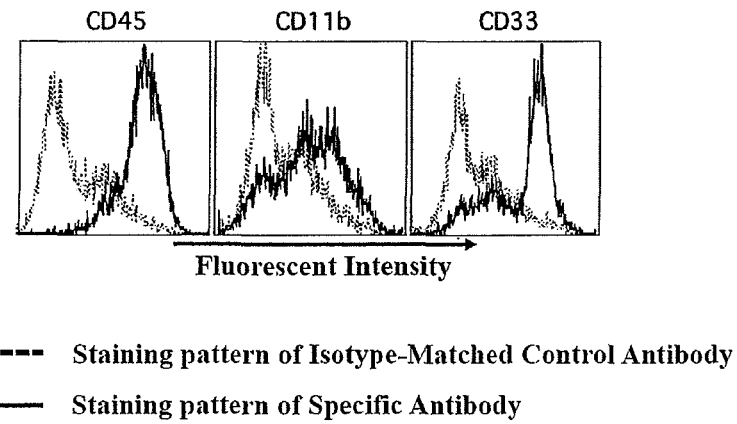
------- Staining pattern of Isotype-Matched Control Antibody
——— Staining pattern of Specific Antibody
FIG. 23 CELL-SURFACE MOLECULE OF HUMAN iPS-ML
BY FORCED EXPRESSION OF cMYC AND BMI1
(WITHOUT USE OF FEEDER CELL)
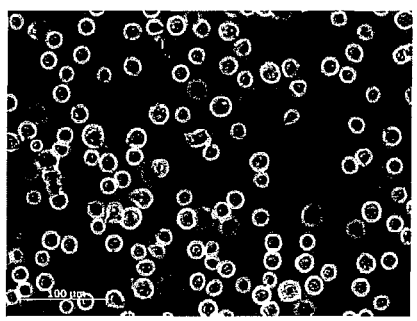
FIG. 24 MORPHOLOGY OF HUMAN MONOCYTE-DERIVED
MYELOID BLOOD CELL LINE (Mo-ML)
GENERATED BY FORCED EXPRESSION OF cMYC AND BMI1

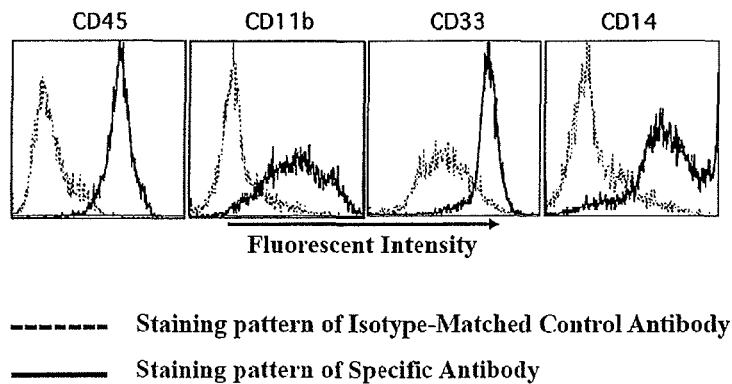
FIG. 25 CELL-SURFACE MOLECULE OF HUMAN MONOCYTE-DERIVED MYELOID BLOOD CELL LINE (MO-ML) GENERATED BY FORCED EXPRESSION OF cMYC AND BMI1
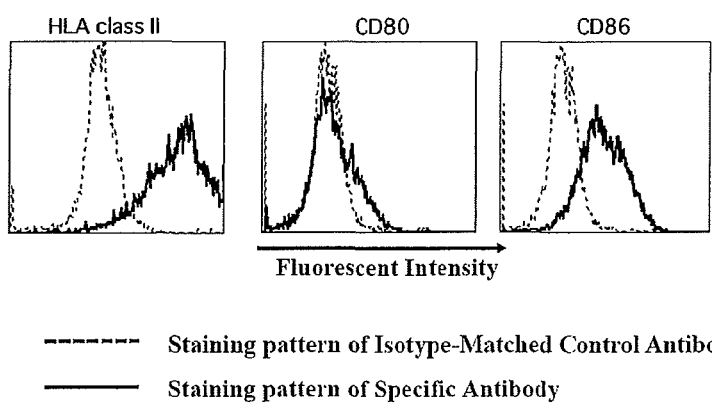
FIG. 26 CELL-SURFACE MOLECULE OF DENDRITIC CELL (CD14ML-DC) DERIVED FROM HUMAN MONOCYTE-DERIVED MYELOID BLOOD CELL LINE

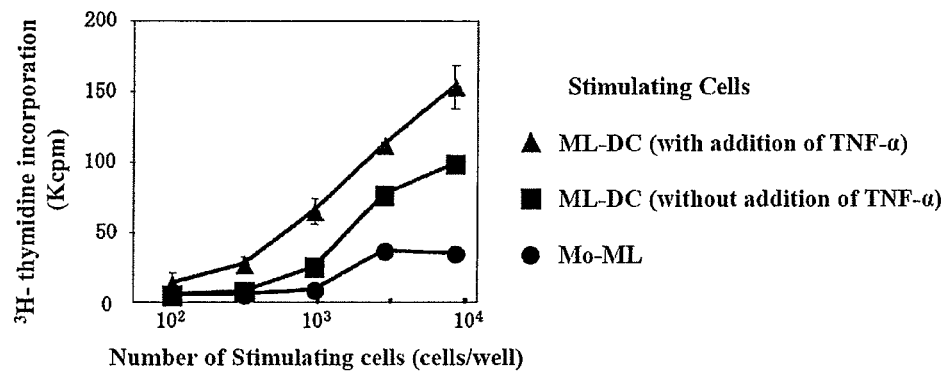
FIG. 27 INDUCTION OF PROLIFERATION REACTION OF ALLO-T CELL BY ML-DC
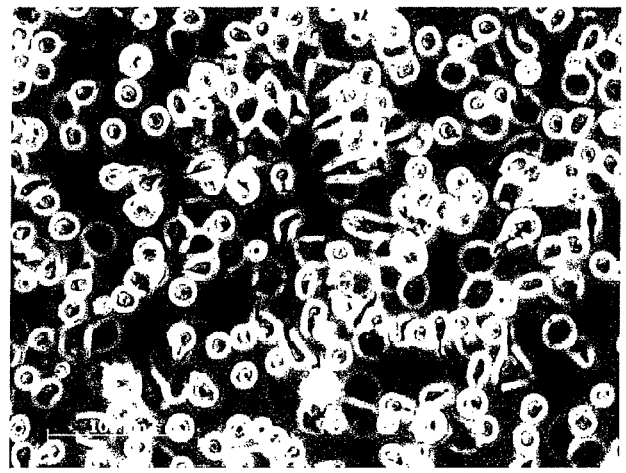
FIG. 28 MORPHOLOGY OF HUMAN MONOCYTE-DERIVED Mo-ML GENERATED BY FORCED EXPRESSION OF cMYC AND MDM2

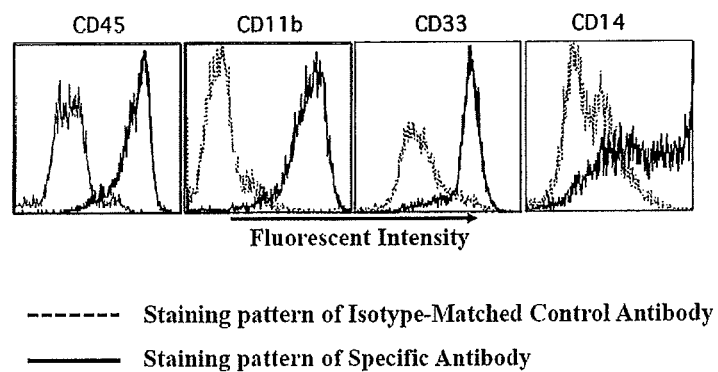
------- Staining pattern of Isotype-Matched Control Antibody
——— Staining pattern of Specific Antibody
FIG. 29 CELL-SURFACE MOLECULE OF HUMAN MONOCYTE-DERIVED MYELOID BLOOD CELL LINE (MO-ML) GENERATED BY FORCED EXPRESSION OF cMYC AND MDM2
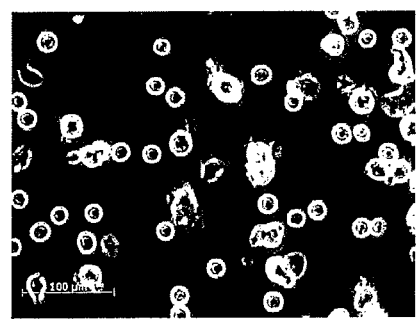
FIG. 30 MORPHOLOGY OF HUMAN MONOCYTE-DERIVED Mo-ML GENERATED BY FORCED EXPRESSION OF cMYC, EZH2 AND MDM2

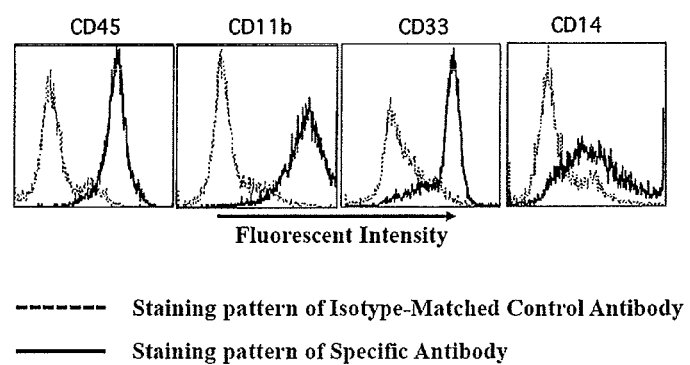
FIG. 31 CELL-SURFACE MOLECULE OF HUMAN MONOCYTE-DERIVED
MYELOID BLOOD CELL LINE (MO-ML)
GENERATED BY FORCED EXPRESSION OF cMYC, EZH2 AND MDM2

METHOD OF PRODUCING MYELOID BLOOD CELLS

TECHNICAL FIELD

The present invention relates to a method of producing human myeloid blood cells that possess a capability of proliferating ex vivo, and to a culturing method thereof. More specifically, the present invention relates to a method of causing myeloid blood cells which are collected from the human body, or myeloid blood cells which are created from pluripotent stem cells, such as artificial pluripotent stem cells, ex vivo by employing a prescribed differentiation induction method, to acquire a capability of proliferating ex vivo while retaining their functions. Furthermore, the present invention relates to a method of differentiating said myeloid blood cells possessing a proliferative capability into dendritic-cell-like cells that possess a stronger T-cell-stimulating capability. The myeloid blood cells, possessing a capability of proliferating ex vivo, produced by the method of the present invention possess a phagocytic activity against microorganisms or the like. The myeloid blood cells, possessing a proliferative capability, produced according to the present invention or the dendritic-cell-like cells derived therefrom are expected to be useful in treating Alzheimer's disease, cancer, infectious diseases, prion diseases, amyloidosis, autoimmune diseases, and so forth. The myeloid blood cells, possessing a proliferative capability, produced according to the present invention and the dendritic-cell-like cells derived therefrom are also expected to be useful in treating transplant rejection and graft-versus-host disease (GVHD) in organ transplantation. Furthermore, because myeloid blood cells play important roles in living organisms with respect to the pathophysiology of cancer, immune-related diseases, metabolic diseases, vascular diseases, and so forth, the myeloid blood cells possessing a proliferative capacity produced according to the present invention are also expected to be useful as test cells in performing pharmacometrics and toxicological assessment for pharmaceuticals, and so forth.

BACKGROUND ART

Myeloid blood cells are a group of cells classified as white blood cells, including macrophages, dendritic cells, granulocytes, and so forth. Macrophages are the major cells that handle foreign substances in a living organism and have a role of defending the living organism from infectious diseases by phagocytosing and degrading infectious microorganisms or the like that have invaded the living organism. In addition, cell deaths occur daily in a large number in a living organism, and macrophages phagocytose and degrade debris thereof existing in the tissue of the living organism. In addition to these, macrophages also play an essential role in homeostatic maintenance of a living organism by processing various metabolites generated in the living organism by means of phagocytosis and degradation thereof. Additionally, it is recognized that macrophages often locally infiltrate malignant tumors. It is thought that there are cases in which macrophages locally existing in tumors attack the tumor cells, as well as cases in which they facilitate proliferation of the tumor cells. In the past, there have also been attempts to treat malignant tumors by utilizing the ability of macrophages to attack tumor cells.

Dendritic cells are cells that activate T lymphocytes by strongly stimulating them, and they are cells that regulate the immune response in living organisms. When infectious microorganisms invade a living organism, the dendritic cells phagocytose the microorganisms, provide the T lymphocytes with antigenic substances derived therefrom, and induce an immune response by stimulating and activating antigen-specific T lymphocytes. There have been attempts to employ dendritic cells as cell vaccines in immunotherapy against cancers and infectious diseases by utilizing the ability of the dendritic cells to strongly stimulate T lymphocytes.

In order to utilize macrophages or dendritic cells as cell drugs, thereby achieving clinical effects, a large number of cells are required. In the case of macrophages, about $10^{10}$ to $10^{12}$ of cells are required while, in the case of dendritic cells, $10^8$ to $10^9$ of cells are required. The number of these cells that exist in a living organism is limited, and also, it is difficult to collect a large number of these cells from a tissue in a living organism. Thus, in order to realize cell therapy by means of macrophages or dendritic cells, it is necessary to establish a method which can stably supply such myeloid blood cells in a large number and at a lower cost.

Macrophages and dendritic cells are cells that play important roles in pathophysiology of cancer, immune-related diseases, metabolic diseases, vascular diseases, and so forth. In developing various pharmaceuticals to treat these diseases, it is necessary to assess effects of drugs on macrophages and dendritic cells. In order to compare effects of many types of pharmaceutical-candidate chemical substances under the same conditions, a method of supplying a large number of macrophages or dendritic cells, possessing uniform characteristics, is required.

Pluripotent stem cells, such as embryonic stem cells (ES cells) or artificial pluripotent stem cells (induced pluripotent stem cells, i.e., iPS cells), are cells that possess an ability to differentiate into various cells, and said cells also possess an ability to proliferate nearly unlimitedly. Meanwhile, methods of creating myeloid blood cells, which have a certain functional similarity with macrophages or dendritic cells existing in living organisms, from pluripotent stem cells have been reported (for example, see Patent Literature 1, and Non-Patent Literatures 1-9). Therefore, it may be theoretically possible to create a large number of myeloid blood cells by proliferating a large number of pluripotent stem cells and by then differentiating them by use of such differentiation induction methods. For example, Patent Literature 1 discloses a method of differentiating human embryonic stem cells into dendritic cells, including (A) a step of co-culturing the human embryonic stem cells and cells, possessing properties of inducing differentiation and proliferation of blood cells, to obtain a cell group A; (B) a step of co-culturing the cell group A obtained in the above step (A) and the cells, possessing properties of inducing differentiation and proliferation of blood cells, in the presence of a granulocyte-macrophage colony stimulating factor (GM-CSF) and a macrophage colony stimulating factor (M-CSF) to obtain a cell group B; and (C) a step of culturing the cell group B obtained in the above step (B) in the presence of GM-CSF and interleukin-4 (IL-4). However, including the differentiation method disclosed in Patent Literature 1, differentiation induction culturing methods that have been reported in the past require considerable effort and time (one month or longer), and therefore, the cost and time requirements are excessive for methods of creating myeloid blood cells for the purpose of using them in cell therapy. In addition, in the past, there has been no report of a method which allows myeloid blood cells, created through differentiation induction of pluripotent stem cells, to proliferate for an extended period of time (for one month or longer) and which makes it possible to create a large number of myeloid blood cells (for example, $10^5$ times or more of the number of pluripotent stem cells used as the starting materials).

Meanwhile, there have been well-known methods of creating dendritic cells and macrophages from monocytes in human peripheral blood (cells which express CD14 molecules in the peripheral blood). Since about 20,000 to 50,000 monocytes exist in 1 mL of peripheral blood of healthy humans, it is possible to separate monocytes from human peripheral blood by use of an indicator of expression of CD 14 molecules and to thus create dendritic cells and macrophages by using them. However, as it is difficult to proliferate human peripheral monocytes through ex vivo culturing, $10^{10}$ monocytes are required to create $10^{10}$ dendritic cells or macrophages, and, to obtain such a number of monocytes, it is required to separate monocytes from about 20 L of peripheral blood. Accordingly, at present, in the case of creating dendritic cells for performing cell vaccine therapy against cancers, white-blood-cell separation by means of cell separation using a blood-component collection device (apheresis) and, additionally, separation of monocytes among the white blood cells have been performed. In addition, there has been a problem in which it is difficult to stably create dendritic cells because large differences exist among donors in terms of the number of monocytes in peripheral blood and the ability thereof to differentiate ex vivo.

Patent Literature 1: PCT International Publication No. WO 2008/056734

Non-Patent Literature 1: Fairchild, P. J, Brook, F A, Gardner, R L, Graca, L, Strong, V, Tone, Y, Tone, M, Nolan, K F, Waldmann, H.2000 Directed differentiation of dendritic cells from mouse embryonic stem cells. Curr Biol. 10:1515-1518.

Non-Patent Literature 2: Lindmark, H, Rosengren, B, Hurt-Cmejo, E, and Bruder, C E. 2004. Gene expression profiling shows that macrophages derived from mouse embryonic stem cells is an improved in vitro model for studies of vascular disease. Exp Cell Res 300:335-344.

Non-Patent Literature 3: Zhan, X, Dravid, G, Ye, Z, Hammond, H, Shamblott, M, Gearhart, J, and Cheng, L. 2004. Functional antigen-presenting leucytes derived from human embryonic stem cells in vitro. Lancet 364:163-171.

Non-Patent Literature 4: Slukvin, II, Vodyanik, M A, Thomson, J A, Gumenyuk, M. E, and Choi, K D. 2006. Directed differentiation of human embryonic stem cells into functional dendritic cells through the myeloid pathway. J Immunol 176:2924-2932.

Non-Patent Literature 5: Odegaard, J I, Vats, D, Zhang, L, Ricardo-Gonzalez, R, Smith, K L, Sykes D B, Kamps, M P, and Chawla, A. 2007. Quantitative expansion of ES cell-derived myeloid progenitors capable of differentiating into macrophages. J Leukoc Biol 81:711-719.

Non-Patent Literature 6: Su, Z, Frye, C, Bae, K M, Kelley, V, and Vieweg, J. 2008. Differentiation of human embryonic stem cells into immunostimulatory dendritic cells under feeder-free culture conditions. Clin Cancer Res 14:6207-6217.

Non-Patent Literature 7: Tseng, S Y, Nishimoto, K P, Silk, K M, Majumdar A S, Dawes, G N, Waldmann, H, Fairchild, P J, Lebkowski, J S, and Reddy, A. 2009. Generation of immunogenic dendritic cells from human embryonic stem cells without serum and feeder cells. Regen Med 4:513-526.

Non-Patent Literature 8: Senju S, Suemori H, Zembutsu H, Uemura Y, Hirata S, Fukuma D, Matsuyoshi H, Shimomura M, Haruta M, Fukushima S, Matsunaga Y, Katagiri T, Nakamura Y, Furuya M, Nakatsuji N, and Nishimura Y. Genetically manipulated human embryonic stem cell-derived dendritic cells with immune regulatory function. Stem cells 25:2720-2729, 2007.

Non-Patent Literature 9: Choi, K D, Vodyanik, M A, and Slukvin, II. 2009. Generation of mature human myelomonocytic cells through expansion and differentiation of pluripotent stem cell-derived lin-CD34+CD43+CD45+ progenitors. J Clin Invest 119:2818-2829.

SUMMARY OF THE INVENTION

An object of the present invention is to provide a method of producing myeloid blood cells possessing a proliferative capability; a method of proliferating said myeloid blood cells; myeloid blood cells obtained by said methods; and a cell drug including said myeloid blood cells. More specifically, an object of the present invention is to provide a method of producing a large number of myeloid blood cells which are useful for cell therapy purposes. Additionally, an object of the present invention is to provide a method of stably producing myeloid blood cells which retain functions equal to myeloid blood cells existing in the human body and which are useful test cells in tests for assaying effects of various pharmaceuticals on myeloid blood cells.

In order to solve the above-described problems, the present inventor has made attempts with various methods to produce a larger number of myeloid blood cells from pluripotent stem cells as inexpensive as possible. In addition, attempts have been made to impart a long-term proliferative capability to myeloid blood cells derived from pluripotent stem cells by forcedly expressing various genes. As a result, it was discovered that, in addition to a cMYC gene, a gene of BMI1, EZH2, MDM2, MDM4 or HIF1A is introduced and forcedly expressed in myeloid blood cells derived from pluripotent stem cells and the cells are continuously culture by using a culture solution to which M-CSF is added, whereby the cells can be proliferated while allowing them to retain characteristics of myeloid blood cells over a long period of time. Furthermore, it is discovered that, even in the case of monocytes in peripheral blood, which are myeloid blood cells existing in the human body, the cells can be proliferated by introducing and forcedly expressing these genes in the cells. The present invention was completed based on the above discoveries.

Specifically, aspects of the present invention relate to the following.

(1) A method of producing a myeloid blood cell possessing a proliferative capability, including forcedly expressing
   (A) a cMYC gene, and
   (B) at least one gene selected from the group consisting of a BMI1 gene, an EZH2 gene, an MDM2 gene, an MDM4 gene, and an HIF1A gene
   in a myeloid blood cell.

(2) The method according to (1), wherein the genes are forcedly expressed in the myeloid blood cell by introducing said genes into said myeloid blood cell.

(3) The method according to (1) or (2), wherein the myeloid blood cell is derived from a pluripotent stem cell.

(4) The method according to (3), wherein the pluripotent stem cell is an artificial pluripotent stem cell.

(5) The method according to (4), wherein the artificial pluripotent stem cell is a human artificial pluripotent stem cell.

(6) The method according to (1) or (2), wherein the myeloid blood cell is a peripheral blood monocyte.

(7) The method according to (6), wherein the peripheral blood monocyte is a human peripheral blood monocyte.
(8) The method according to any one of (1) to (7), wherein the cMYC gene, the BMI1 gene, the EZH2 gene, the MDM2 gene, the MDM4 gene and the HIF1A gene are a human cMYC gene, a human BMI1 gene, a human EZH2 gene, a human MDM2 gene, a human MDM4 gene and a human HIF1A gene, respectively.
(9) A method of proliferating a myeloid blood cell, including culturing the myeloid blood cell produced by the method according to any one of (1) to (8) in the presence of a macrophage colony stimulating factor (M-CSF).
(10) A cell produced by the method according to any one of (1) to (9).
(11) A method of producing a dendritic-cell-like cell, including inducing the myeloid blood cell according to (10) to differentiate into the dendritic-cell-like cell.
(12) The method according to (11), wherein the myeloid blood cell is induced to differentiate into the dendritic-cell-like cell by culturing said myeloid blood cell by use of a culture solution containing a granulocyte-macrophage colony-stimulating factor (GM-CSF) and interleukin-4 (IL-4).
(13) A cell produced by the method according to (11) or (12).
(14) A cell drug containing the cell according to (10) or (13).
(15) The cell drug according to (14), wherein said cell drug is a cell drug for use in treatment or prevention of an infection, a tumor, Alzheimer's disease, a prion disease, amyloidosis, leukemia, and/or an autoimmune disease.
(16) Use of
  (A) a cMYC gene, and
  (B) at least one gene selected from the group consisting of a BMI1 gene, an EZH2 gene, an MDM2 gene, an MDM4 gene, and an HIF1A gene for producing the cell according to (10) or (13), or the cell drug according to (14). (17) A method of treating an infection, a tumor, Alzheimer's disease, a prion disease, amyloidosis, leukemia, and/or an autoimmune disease by use of the cell drug according to (14).

The present invention makes it possible to supply myeloid blood cells, in a large number and also stably, without exerting a physical burden on a cell donor. In addition, the myeloid blood cells produced according to the present invention possess a phagocytic activity against microorganisms or the like in the same manner as macrophages existing in a living organism, and thus, makes it possible to provide cell drugs for performing cell therapy against infectious diseases and malignant tumors. Also, the present invention also makes it possible to provide cell drugs against diseases caused by a large amount of specific substances accumulating in the body, such as Alzheimer's disease, amyloidosis, certain types of metabolic diseases, or the like. Moreover, according to the present invention, it is possible to produce dendritic-cell-like cells that can be used as cell vaccines against malignant tumors, infectious diseases, and so forth. Furthermore, the present invention makes it possible to produce dendritic-cell-like cells or macrophages as cell drugs for regulating immune responses for the purpose of treating autoimmune diseases, transplant rejection involved in organ transplantation, and so forth. Additionally, the present invention makes it possible to stably produce myeloid blood cells which are useful as test cells in tests or research for assaying effects of various pharmaceuticals on myeloid blood cells.

BRIEF DESCRIPTION OF THE DRAWINGS

FIG. 1 is a diagram for summarizing a production method according to the present invention.

FIG. 2 is a micrograph (image captured with a phase-contrast lense) of myeloid blood cells (iPS-MC) derived from human iPS cells.

FIG. 3 shows results of flow cytometric analysis on expressions of CD45, CD1 Ib and CD33 molecules in myeloid blood cells (iPS-MC) derived from human iPS cells.

FIG. 4 is a micrograph (image captured with a phase-contrast lense) of human-iPS-cell-derived myeloid blood cell line (iPS-ML) which was produced by forced expression of cMYC and BMI1.

FIG. 5 shows results of flow cytometric analysis on expressions of CD45, CD11b and CD33 molecules in myeloid blood cell line (iPS-ML) which was produced by forced expression of cMYC and BMI1.

FIG. 6 shows results of investigation on dependency of proliferation of the myeloid blood cell line (iPS-ML) on M-CSF and GM-CSF.

FIG. 7 shows results of investigation on phagocytosis by the myeloid blood cell line (iPS-ML) of fluorescently-labeled zymosan particles.

FIG. 8 shows changes over time in phagocytosis by the myeloid blood cell line (iPS-ML) of fluorescently-labeled zymosan particles.

FIG. 9 is a micrograph of dendritic-cell-like cells (ML-DC) derived from the myeloid blood cell line (iPS-ML).

FIG. 10 shows results of flow cytometric analysis on expressions of HLA Class 11, CD80 and CD86 on the cell surfaces of the dendritic-cell-like cells (ML-DC) derived from the myeloid blood cell line (iPS-ML).

FIG. 11 shows results of investigation on activities of inducing proliferation response of allo-T cells with respect to the myeloid blood cell line (iPS-ML) and the dendritic-cell-like cells (ML-DC) derived therefrom.

FIG. 12 is a micrograph (image captured with a phase-contrast lense) of human-iPS-cell-derived myeloid blood cell line (iPS-ML) which was produced by forced expression of cMYC and EZH2.

FIG. 13 shows results of flow cytometric analysis on expressions of CD45, CD11b, CD33 and CD14 molecules in the myeloid blood cell line (iPS-ML) which was produced by forced expression of cMYC and EZH2.

FIG. 14 is a micrograph (image captured with a phase-contrast lense) of human-iPS-cell-derived myeloid blood cell line (iPS-ML) which was produced by forced expression of cMYC and MDM2.

FIG. 15 shows results of flow cytometric analysis on expressions of CD45, CD11b, and CD33 molecules in the myeloid blood cell line (iPS-ML) which was produced by forced expression of cMYC and MDM2.

FIG. 16 is a micrograph (image captured with a phase-contrast lense) of human-iPS-cell-derived myeloid blood cell line (iPS-ML) which was produced by forced expression of cMYC and MDM4.

FIG. 17 shows results of flow cytometric analysis on expressions of CD45, CD11b, and CD33 molecules in the myeloid blood cell line (iPS-ML) which was produced by forced expression of cMYC and MDM4.

FIG. 18 is a micrograph (image captured with a phase-contrast lense) of human-iPS-cell-derived myeloid blood cell line (iPS-ML) which was produced by forced expression of cMYC and HIF1A.

FIG. 19 shows results of flow cytometric analysis on expressions of CD45, CD11b, and CD33 molecules in the myeloid blood cell line (iPS-ML) which was produced by forced expression of cMYC and HIF1A.

FIG. 20 is a micrograph (image captured with a phase-contrast lense) of human-iPS-cell-derived myeloid blood cells (iPS-MC) produced by a differentiation induction method which does not use any feeder cells.

FIG. 21 shows results of flow cytometric analysis on expressions of CD45, CD11b, and CD33 molecules in the human-iPS-cell-derived myeloid blood cells (iPS-MC) produced by a differentiation induction method which does not use any feeder cells.

FIG. 22 is a micrograph (image captured with a phase-contrast lense) of iPS-ML produced by forcedly expressing cMYC and BMI1 in human-iPS-cell-derived iPS-MC produced by a differentiation induction method which does not use any feeder cells.

FIG. 23 shows results of flow cytometric analysis on expressions of CD45, CD11b, and CD33 molecules in iPS-ML produced by forcedly expressing cMYC and BMI1 in human-iPS-cell-derived iPS-MC produced by a differentiation induction method which does not use any feeder cells.

FIG. 24 is a micrograph (image captured with a phase-contrast lense) of myeloid blood cell line (Mo-ML) which was produced by forced expression of cMYC and BMI1 and which was derived from human peripheral blood monocytes.

FIG. 25 shows results of flow cytometric analysis on expressions of CD45, CD11b, CD33 and CD14 molecules in myeloid blood cell line (Mo-ML) which was produced by forced expression of cMYC and BMI1 and which was derived from human peripheral blood monocytes.

FIG. 26 shows results of flow cytometric analysis on expressions of HLA class II, CD80 and CD86 on cell surfaces of the dendritic-cell-like cells (ML-DC) derived from the myeloid blood cell line (Mo-ML) which was derived from human peripheral blood monocytes.

FIG. 27 shows results of investigation on activities of inducing proliferation response of allo-T cells with respect to the myeloid blood cell line (Mo-ML) and the dendritic-cell-like cells (ML-DC) derived therefrom.

FIG. 28 is a micrograph (image captured with a phase-contrast lense) of myeloid blood cell line (Mo-ML) which was produced by forced expression of cMYC and MDM2 and which was derived from human peripheral blood monocytes.

FIG. 29 shows results of flow cytometric analysis on expressions of CD45 and CD11b molecules in myeloid blood cell line (Mo-ML) which was produced by forced expression of cMYC and MDM2 and which was derived from human peripheral blood monocytes.

FIG. 30 is a micrograph (image captured with a phase-contrast lense) of myeloid blood cell line (Mo-ML) which was produced by forced expression of cMYC, EZH2 and MDM2 and which was derived from human peripheral blood monocytes.

FIG. 31 shows results of flow cytometric analysis on expressions of CD45 and CD11b molecules in myeloid blood cell line (Mo-ML) which was produced by forced expression of cMYC, EZH2 and MDM2 and which was derived from human peripheral blood monocytes.

EMBODIMENT FOR CARRYING OUT THE INVENTION

As shown in FIG. 1, the present invention is characterized by allowing myeloid blood cells which are defined cells expressing a CD11b molecule or a CD33 molecule, e.g. myeloid blood cells derived from pluripotent stem cells, or myeloid blood cells which are collected directly from a living organism, to acquire a capability of proliferating ex vivo.

In order to allow the above-described cells to acquire a capability of proliferating ex vivo, the present invention is characterized by including forcedly expressing (A) a cMYC gene, and (B) at least one gene selected from the group consisting of a BMI1 gene, an EZH2 gene, an MDM2 gene, an MDM4 gene, and an HIF1A gene in a myeloid blood cell.

In the present invention, "myeloid blood cell(s)", which is a starting material, are defined as cells expressing a CD11b molecule or a CD33 molecule. Although their origin is not particularly limited, for example, myeloid blood cells derived from pluripotent stem cells, or myeloid blood cells (e.g. peripheral blood monocytes) which are collected directly from a living organism (e.g. human body) can be mentioned.

In the present invention, a "pluripotent stem cell" refers to a cell that possesses proliferative capacity under artificially generated conditions, such as in a test tube (in vitro), and that is capable of differentiating into any cells forming a living organism. In the present invention, it is preferable that an embryonic stem cell or an artificial pluripotent stem cell (an induced pluripotent stem cell, i.e., an iPS cell) be used as the pluripotent stem cell, and it is more preferable that an artificial pluripotent stem cell be used. The embryonic stem cell and the artificial pluripotent stem cell used in the present invention will be described below.

(Embryonic Stem Cell)

The embryonic (ES) cell used in the present invention is not particularly limited in terms of the type thereof etc., so long as the ES cell is of mammalian origin. For example, an ES cell of mouse origin, monkey origin or human origin, or the like can be used. For example, a human embryonic (ES) cell is a stem cell which is established from a human embryo, and is a cell which can proliferate ex vivo over a long period of time while maintaining the capability of differentiating into any cells existing in a living organism (i.e. pluripotent differentiation).

(Artificial Stem Cell)

The iPS cell used in the present invention is a cell which has been allowed to acquire pluripotent differentiation by applying an artificial manipulation to a somatic cell. The type of somatic cell to be used herein is not particularly limited, and any somatic cell forming a living body are included.

The iPS cell mentioned in the present invention refers to a stem cell that possesses a self-replicating capacity for a long period of time under prescribed culturing conditions (for example, under the conditions for culturing ES cells) and that further possesses multipotency to differentiate into ectoderm, mesoderm, and endodemi under prescribed differentiation induction conditions. In addition, the artificial pluripotent stem cell in the present invention may be a stem cell possessing the ability to form a teratoma when transplanted to a test animal such as a mouse.

In order to produce an iPS cell from a somatic cell, at first, at least one or more types of reprogramming genes are introduced into the somatic cell. The reprogramming gene is a gene that codes for a reprogramming factor that has a reprogramming effect on a somatic cell to form an iPS cell.

Although combinations of reprogramming genes include the following specific examples, it is not limited thereto.
(i) an Oct gene, a Klf gene, a Sox gene, and a Myc gene;
(ii) an Oct gene, a Sox gene, a NANOG gene, and a L1N28 gene;
(iii) an Oct gene, a Klf gene, a Sox gene, a Myc gene, an hTERT gene, an SV40 large T gene; and
(iv) an Oct gene, a Klf gene, and a Sox gene An Oct gene, a Klf gene, a Sox gene, and a Myc gene each include a plurality of family genes. As specific examples of the individual family genes, those described on pages 11 to 13 of the Specification of PCT International Publication No. WO2007/069666 can be used. Specifically, they are as follows.

Specific examples of genes belonging to the Oct gene include Oct3/4 (NM_002701), Oct1A (NM_002697), Oct6 (NM_002699) and so forth (the numbers in the parentheses indicate NCBI accession numbers for human genes). Oct3/4 is preferable. Oct3/4 is a transcription factor belonging to the POU family, is known to be an undifferentiation marker, and is also reported to be involved in maintaining pluripotency.

Specific examples of genes belonging to the Klf gene include Klf1 (NM_006563), Klf2 (NM_016270), Klf4 (NM_004235), Klf5 (NM_001730), and so forth (the numbers in the parentheses indicate NCBI accession numbers for human genes). Klf4 is preferable. Klf4 (Kruppel-like factor-4) is reported to be a tumor inhibitory factor.

Specific examples of genes belonging to the Sox gene include Sox1 (NM_005986), Sox2 (NM_003106), Sox3 (NM_005634), Sox7 (NM_031439), Sox15 (NM_006942), Sox17 (NM_0022454), Sox18 (NM_018419) and so forth (the numbers in the parentheses indicate NCBI accession numbers for human genes). Sox2 is preferable. Sox2 is expressed in the initial developmental process and is a gene coding for a transcription factor.

Specific examples of genes belonging to the Myc gene include c-Myc (NM_002467), N-Myc (NM_005378), L-Myc (NM_005376), and so forth (the numbers in the parentheses indicate NCBI accession numbers for human genes). c-Myc is preferable. c-Myc is a transcription regulation factor involved in differentiation and proliferation of cells and is reported to be involved in maintaining pluripotency.

The above-described genes are genes that commonly exist in mammals, including humans, and, in the present invention, it is possible to use genes of any mammalian origin (for example, having their origin in mammals, such as humans, mouse, rat, monkey, and so forth). In addition, it is also possible to use mutated genes that have several nucleotides (for example, 1 to 30, preferably 1 to 20, more preferably 1 to 10, even more preferably 1 to 5, and particularly preferably 1 to 3) replaced, inserted, and/or deleted with respect to wild-type genes and that are genes possessing the same functions as the wild-type genes.

As the reprogramming genes, a combination of the Oct3/4 gene, the Klf4 gene, the Sox2 gene, and the c-Myc gene can particularly preferably be used in the present invention.

The method of introducing the reprogramming genes into the somatic cell is not particularly limited so long as the introduced reprogramming genes can be expressed in the somatic cell to achieve reprogramming thereof. For example, the reprogramming genes can be introduced into the somatic cell by using an expression vector including at least one or more types of reprogramming genes. When introducing two or more types of reprogramming genes into the somatic cell by using a vector, two or more types of reprogramming genes may be incorporated into a single expression vector, and said expression vector may be introduced into the somatic cell; alternatively, two or more types of expression vectors into each of which one type of reprogramming gene is incorporated may be prepared, and these may be introduced into the somatic cell.

The type of expression vector is not particularly limited, and it may be a viral vector or a plasmid vector. As examples of viral vectors which can be used for production of induced pluripotent stem cells, a retrovirus vector (including a lentivirus vector), an adenovirus vector, an adeno-associated virus vector, a sendai virus vector, and so forth can be mentioned.

A recombinant viral vector can be produced by introducing a recombinant viral vector plasmid into a packaging cell. The method of introducing the above-described virus vector plasmid into the packaging cell is not particularly limited, and the gene introduction can be performed by means of a known gene-introduction method such as calcium phosphate transfection, lipofection, electroporation, or the like.

In this field, there are known media which can maintain undifferentiated properties and pluripotency of the ES cell, and the artificial pluripotent stem cell of the present invention can be separated and cultured by using appropriate media in combination. Specifically, as examples of media for culturing the artificial pluripotent stem cell of the present invention, an ES medium, an MEF-conditioned ES medium, which is a supernatant of a culture which is obtained by adding 10 ng/mL of FGF-2 to an ES medium and by then culturing mouse embryonic fibroblasts therein for 24 hours (hereinafter referred to as the MEF-conditioned ES medium), and so forth. Various growth factors, cytokines, hormones, and so forth (for example, ingredients that are involved in proliferation and maintenance of human ES cells, such as FGF-2, TGFb-1, activin A, noggin (Nanoggin), BDNF, NGF, NT-1, NT-2, NT-3, and so forth) may be added to the medium for culturing the artificial pluripotent stem cell of the present invention. In addition, the differentiation capacity and the proliferative capacity of a separated artificial pluripotent stem cell can be confirmed by utilizing a known confirmation method for the ES cell.

(Differentiation of a Pluripotent Stem Cell into a Myeloid Blood Cell)

In the present invention, a "myeloid blood cell derived from a pluripotent stem cell" is a cell which is produced by inducing differentiation of the pluripotent stem cell while culturing them ex vivo, and refers to a cell which expresses CD11b or CD 33 molecule, which is a marker molecule for myeloid blood cells, on the cell surface. Methods of differentiating a human pluripotent stem cell into a myeloid blood cell have been known in this field. For example, non-patent literatures 6, 7, 8 and 9 describes methods of producing dendritic cells or macrophages, which are myeloid blood cells, from human pluripotent stem cells. Hereinafter, examples of the method of differentiating the pluripotent stem cell into the myeloid blood cell will specifically be described below. However, the present invention is not necessarily limited to the myeloid blood cell derived from the pluripotent stem cell produced by means of differentiation induction according to the method described below.

(A method of Inducing Differentiation of a Pluripotent Stem Cell into a Myeloid Blood Cell)

A cell possessing a property of inducing differentiation and proliferation of blood cells is used as a feeder cell, and a pluripotent stem cell and said feeder cell are co-cultured, whereby the pluripotent stem cell can be differentiated into a cell group including mesodermal cells.

As the "cell possessing a property of inducing differentiation and proliferation of the blood cell", for example, an OP9 cell (RIKEN BioResource Center Deposit No. RCB 1124) can be used.

The "cell possessing a property of inducing differentiation and proliferation of the blood cell" may be cultured in a culture vessel containing an appropriate medium under culturing conditions appropriate for said feeder cell, and may be proliferated to the degree that the cells nearly cover the bottom surface of the culture vessel, and the cell proliferation may be stopped by means of treatment with a mitomycin C solution or exposure to radiation, and then, the cells may be again transferred to a separately prepared cell culture vessel to form a feeder cell layer, and this may be used therein. The above-described pluripotent stem cell can be inoculated on the feeder cells prepared in this way, and thus, co-culturing can be carried out.

With regard to media used for the above-described preparation of feeder cells and the co-culturing, a medium appropriate for culturing adherent mammalian cells may be used, and is appropriately selected in accordance with the type etc. of the feeder cells. For example, aMEM, DMEM (Dulbecco's Modified Eagle's Medium), IMDM (Iscove's Modified Dulbecco's Medium), and so forth can be mentioned.

With regard to the culturing conditions for the above-described feeder cells, they can be appropriately set in accordance with the type etc. of the cells used as the feeder cells. For example, in the case of the OP9 cells or the like, conditions in which they are cultured on a culture vessel coated with a 0.1 wt % gelatin solution can be mentioned.

With regard to gas-phase conditions for the co-culturing described above, they can be appropriately set in accordance with the type of the pluripotent stem cells used therein. For example, about 37° C. (37° C. in particular), 5 vol. % $CO_2$, and so forth can be mentioned.

The cell group obtained by the above-described co-culturing exhibits properties of mesodermal cells, and can be obtained in the form of a cell group including cell clumps having an approximately spherical shape.

It is preferable that a cell population which contains a large number of cells having been derived from the pluripotent stem cells and having differentiated into mesodermal cells in particular be separated from the co-cultured products of the pluripotent stem cells and the feeder cells, and that the separated cell population be used in the later steps. With regard to methods of separating differentiated mesodermal cells, a method in which cells recovered after the co-culturing are allowed to stand in a culture vessel to remove cells having strong adherability, whereby mesodermal cells, which are cells having weak adherability, are harvested can be mentioned. For example, the above-described co-cultured products may be treated with enzymes such as trypsin, collagenase, and so forth; all cells are recovered; they are diluted with an appropriate medium such as DMEM to an appropriate volume; and, subsequently, the cell solution is inoculated into a newly prepared culture vessel. Two to five hours after the inoculation, cells that have adhered to the culture vessel are discarded, and thus, the cells which did not adhere thereto, but are present in the medium, can be recovered as the cell population containing a large number of mesodermal cells. In addition, it is preferable that cell clumps of 100 μm or larger contained in the recovered cell suspension be removed by using a nylon mesh (for example, the 100-μm nylon cell strainer manufactured by B. D. Falcon) or the like.

Subsequently, the cell group containing the mesodermal cells obtained as described above are cultured in the presence of granulocyte-macrophage colony stimulating factor (GM-CSF) and/or macrophage colony stimulating factor (M-CSF), whereby said mesodermal cells can be differentiated into myeloid blood cells. The media, culturing conditions, and so forth that can be used for differentiating the cell group containing mesodermal cells into myeloid blood cells are not particularly limited, and it is possible to use media, culturing conditions, and so forth that are the same as those used in culturing and co-culturing of the feeder cells described above.

From the viewpoint of promoting the differentiation of the mesodermal cells into the myeloid blood cells, the amount of the granulocyte-macrophage colony stimulating factor (GM-CSF) contained in the medium can be set within a range from 50 to 200 ng/mL, or preferably 75 to 150 ng/mL. In addition, from the viewpoint of promoting the differentiation of the mesodermal cells into the myeloid blood cells, the amount of macrophage colony stimulating factor (M-CSF) contained in the medium can be set within a range from 10 to 100 ng/mL, or preferably 25 to 75 ng/mL.

The culturing period required for the differentiation of the mesodermal cells into the myeloid blood cells is not limited according to culturing conditions or the like, and for example, it may be about 1 to 30 days, or preferably about 2 to 15 days.

With regard to culturing methods of inducing differentiation of pluripotent stem cells into myeloid blood cells, a method not using feeder cells, or a method using a culture solution not containing serum derived from animals may also be used, as described in non-patent literature 6 or 7. Hereinafter, one example of a method of differentiating pluripotent stem cells into myeloid blood cells not using feeder cells but using a culture solution not containing serum derived from animals will be specifically explained. In addition, some culturing methods of inducing differentiation of pluripotent cells into myeloid blood cells without use of feeder cells, other than the methods explained herein, have been known, as described in non-patent literature 6 or 7. Myeloid blood cells used in the present invention are not limited to myeloid blood cells derived from pluripotent stem cells, said myeloid blood cells produced by differentiation induction according to any of methods.

(Example of Inducing Differentiation of Pluripotent Stem Cells into Myeloid Blood Cells Without Use of Feeder Cells)

When carrying out the differentiation induction using neither feeder cells nor serums from non-human animals, a culture vessel which is coated with a fibronectin or the like can be used in order to assist the cells to adhere to the culture vessel. With regard to the fibronectin used for coating the culture vessel, those purified from human serum, or a human fibronectin prepared as a gene recombinant protein can be used.

When using a culture solution not containing a serum from non-human animals, those prepared by adding serum replacement additives, such as KSR (Life Technology) or Peprogrow III (Peprotech), to D-MEM (Dulbecco's Modified Eagle's Medium), aMEM (Alpha-Minimum Essential Medium) or the like; or commercially-available serum-free culture solution (AIM-V, OpTmizer: Life Technology, Stemline: Sigma) can be used.

Human pluripotent stem cells are cultured in a human fibronectin-coated culture vessel for 15 to 20 days by use of a culture solution not containing serums from animals. Additionally, human BMP-4 (Bone Morphogenic Protein 4)

may be added to the culture solution not containing serums from animals in order to promote differentiation of the pluripotent stem cells.

When carrying out the culturing for differentiation induction, differentiated cells of various cell lineages emerge. Therefore, it is preferable that cells that have differentiated into mesodermal cells be separated from these cells, and that the separate cells be used as the cell group containing mesodermal cells in the later steps. With regard to methods of separating the differentiated mesodermal cells, a method in which cells recovered after co-culturing are allowed to stand in a culture vessel to remove adhered cells, whereby a cell population containing a large number of mesodermal cells, which are floating cells, can be mentioned, in the same manner as the case of differentiation induction methods using feeder cells.

Subsequently, the cell group containing a large number of mesodermal cells obtained as described above are cultured in the presence of a granulocyte-macrophage colony stimulating factor (GM-CSF) and/or a macrophage colony stimulating factor (M-CSF), whereby said mesodermal cells can be differentiated into myeloid blood cells. The media, culturing condition, etc. used for differentiating the cell group containing mesodermal cells into myeloid blood cells are not particularly limited, and various types of serum-free culture solution can be used therefor.

In the present invention, myeloid blood cells that are present in a living organism (e.g. in the human body) can also be used. With regard to the myeloid blood cells present in a living organism, for example, peripheral blood monocytes can be used, and it is preferable that human peripheral blood monocytes be used. Hereinafter, as one example of a method of obtaining myeloid blood cells that are present in a living organism, a method of separating monocytes from human peripheral blood will be explained. However, methods of obtaining myeloid blood cells used in the present invention are not limited to this method.

(Separation of Monocytes from Human Peripheral Blood)

Human peripheral blood is collected from the body. As an anticoagulant, heparin, citric acid, or the like may be used. The collected blood is diluted with an equal amount of physiological saline, phosphate buffered saline, a Hanks' balanced salt solution, or the like. Then, the diluted blood is layered on a ficoll solution (GE Healthcare) which have been dispensed into centrifuge tubes (BD-Falcon 352070, etc.) in advance. Subsequently, this is centrifuged for twenty minutes at a centrifugal force of 500 g by use of a centrifugal apparatus, and a fraction of mononuclear cells (containing lymphocytes and monocytes) which are present around the boundary face is collected.

Monocytes can be separated from the mononuclear cells by use of magnetic-bead technique or the like by assessing expression of a CD14 molecule. For example, CD14 microbeads (manufactured by Miltenyi Biotec K.K., 130-050-201), etc. can be used to separate the monocytes. Alternatively, the fraction of mononuclear cells may be cultured for about 6 to 16 hours using a culture vessel which has been subjected to a surface treatment for cell culturing, and the cells which have adhered to the vessels can be recovered, thereby obtaining monocytes or macrophages derived therefrom. In general, 200,000 to 500,000 monocytes can be harvested from 10 mL of peripheral blood of a health adult.

(Imparting Long-Term Proliferative Capability to Myeloid Blood Cells Derived from Pluripotent Stem Cells)

In the present invention, a cMYC gene; and at least one gene selected from the group consisting of a BMI1 gene, an EZH2 gene, an MDM2 gene, an MDM4 gene, and an HIF1A gene are forcedly expressed in a myeloid blood cell derived from a pluripotent stem cell or in a myeloid blood cell collected from a living body, thereby imparting a long-term proliferative capability to these cells. With regard to a method of forcedly expressing the above genes, an endogenous genes existing in the myeloid-blood-cell genome may be forcedly expressed; alternatively, these genes may be forcedly expressed by introducing exogenous genes into the myeloid blood cell. From the viewpoint of achieving efficient and high-level expression of the genes and reliably imparting a long-term proliferative capability to the myeloid blood cell, a method in which the exogenous genes are introduced into the myeloid blood cell by using genetic engineering techniques is preferable.

In the present invention, the "myeloid blood cell having a proliferative capability" refers to a myeloid blood cell to which a long-term proliferative capability has been imparted by forcedly expressing the above genes in said myeloid blood cell, as described above. The "myeloid blood cell having a proliferative capability" of the present invention can proliferate over an extended period of time, compared to a control myeloid blood cell to which the above genes have not been introduced (e.g. myeloid blood cells used as the starting material), and, for example, can proliferate for two weeks or more from the time point when the above genes are forcedly expressed therein (the time point when the above genes are introduced to the cell).

With regard to specific examples of the cMYC gene, the human cMYC gene (NM_002467) used in preparing the above-described artificial pluripotent stem cells can be mentioned (the number in the parenthesis indicates the NCBI accession number). In addition, as specific examples of the BMI1 gene, the EZH2 gene, the MDM2 gene, the MDM4 gene and the H1F1A gene, a human BMI1gene (NM_005180), a human EZH2 gene (NM_004456), a human MDM2 gene (NM_002392), a human MDM4 gene (NM_002393), a human HIF1A gene (NM_001530) can be mentioned (the number in the parenthesis indicates the NCBI accession number).

The cMYC gene, the BMI1 gene, the EZH2 gene, the MDM2 gene, the MDM4 gene and the HIF1A gene are genes that commonly exist in mammals, including humans, and genes of any mammalian origin (for example, having their origin in mammals, such as human being, mouse, rat, monkey or the like) can be used in the present invention. Moreover, it is also possible to use a mutated gene which has several nucleotides (for example, 1 to 30, preferably 1 to 20, more preferably 1 to 10, even more preferably 1 to 5, and particularly preferably 1 to 3) replaced, inserted, and/or deleted with respect to the wild-type gene and which further possess the same function as the wild-type genes. Furthermore, a gene which have been artificially modified so as to be expressed as a fusion protein of said gene product with another protein or peptide, as long as it possesses the equivalent or superior functions as compared to the wild-type gene.

The method of introducing the cMYC, BMI1, EZH2, MDM2, MDM4 and HIF1A genes into the above-described myeloid blood cell is not particularly limited so long as these introduced genes are expressed therein so as to impart a long-term proliferative capability to the myeloid blood cell. For example, these genes can be introduced into the myeloid blood cell by using an expression vector(s) including said genes. In addition, a plurality of genes may be incorporated into one expression vector, and said expression vector may be introduced into the myeloid blood cell; alternatively, expression vectors into which each gene is separately incorporated may be prepared, and these may be introduced into the myeloid blood cell.

The type of expression vector is not particularly limited, and it may be a viral vector or a plasmid vector; however, a viral vector is preferable, and a viral vector which incorporates the transfected gene(s) into a chromosome of the myeloid blood cell is particularly preferable. As viral vectors that can be used in the present invention, a retrovirus vector, a lentivirus vector, an adeno-associated virus vector, and so forth can be mentioned.

With regard to packaging cells used for preparing the recombinant virus vector, any cell can be used as long as said cell can supply at least one protein of gene, said gene being deficient in a recombinant virus vector plasmid, in which said gene encodes for a protein required for viral packaging. For example, a packaging cell based on the HEK293 cell derived from human kidney or the mouse fibroblast NII-13T3 can be used.

The recombinant viral vector can be produced by introducing the recombinant viral vector plasmid into the packaging cell. The method of introducing the above-described virus vector plasmid into the packaging cell described above is not particularly limited, and can be performed by means of a known method such as calcium phosphate transfection, lipofection, electroporation or the like. Furthermore, a solution in which the gene recombinant virus is concentrated can be recovered from the culture supernatant of packaging cells having the plasmid introduced therein by means of a centrifugation method or a concentration method using a commercially-available column for virus purification.

The solution containing the gene recombinant virus as prepared above is added to the myeloid blood cells derived from pluripotent stem cells or to the myeloid blood cells collected directly from the human body in a culture vessel to infect the virus thereto, thereby introducing the genes of interest thereto.

(A Method of Proliferating a Myeloid Blood Cell Possessing a Proliferative Capability)

The myeloid blood cells possessing a capability of proliferating ex vivo, as produced above, can be cultured in a cell culture solution containing M-CSF. The amount of macrophage colony stimulating factor (M-CSF) contained in the culture solution can be set within a range from 25 to 100 ng/mL. Alternatively, an M-CSF gene may be introduced into the myeloid blood cells themselves by means of a lentivirus vector or the like, whereby the myeloid blood cells themselves can be allowed to produce M-CSF. In this case, the cells can be cultured and proliferated in a cell culture solution to which M-CSF has not been added.

(Differentiation of Myeloid Blood Cells into Dendritic-Cell-Like Cells)

Dendritic-cell-like cells can be produced from the myeloid blood cells of the present invention possessing a capability of proliferating ex vivo. For example, dendritic-cell-like cells can be produced by culturing the myeloid blood cells of the present invention possessing a long-term proliferative capability in the presence of GM-CSF and interleukin4 (IL-4). The amount of GM-CSF contained in the culture solution can be set within a range from 50 to 200 ng/mL while the amount of IL-4 contained therein can be set within a range from 5 to 20 ng/mL. In the present invention, the "dendritic-cell-like cell" refers to a cell possessing properties similar to a monocyte-derived dendritic cell or the like in terms of morphology, cell-surface molecules, and T-cell stimulation ability.

(Cell Drugs)

In the same manner as macrophages etc. existing in living organisms, the myeloid blood cells of the present invention possess a phagocytic activity against microorganisms or the like, and they can provide cell drugs for performing immuno-cell therapy against infectious diseases and malignant tumors. In addition, the myeloid blood cells of the present invention can also provide cell drugs for use in treating diseases or the like caused by a large amount of specific substances accumulating in the body, such as Alzheimer's disease, priori diseases, amyloidosis, cancers, leukemia, or certain types of metabolic diseases. Also, the dendritic-cell-like cells of the present invention derived from the myeloid blood cells possessing a long-term proliferative capability can be used as cell vaccines for use in treating malignant tumors and infectious diseases. Furthermore, the dendritic-cell-like cells of the present invention derived from the myeloid blood cells can provide cell drugs for use in controlling an immune response for the purpose of treating autoimmune diseases, transplant rejection involved in organ transplantation, and so forth.

When producing cell drugs of the present invention, auxiliary agents, for example, culture media and so forth, other than those described above may be appropriately used for the purpose of enabling stable retention of the myeloid blood cells of the present invention possessing a long-term proliferative capability and myeloid blood cells derived therefrom.

The present invention will be more specifically described by means of the following examples. However, the present invention is not particularly limited by the following examples.

EXAMPLES

Example 1: Production of Lentivirus Vectors cDNAs of human OCT3/4, SOX2, KLF4, and c-MYC, which are reprogramming factors, were synthesized by means of PCR, and cloning was performed by inserting them into plasmid vectors (pENTR-D-TOPO, Gibco-Invitrogen). Then, nucleotide sequences of the cloned plasmid DNAs were confirmed by means of sequence analysis. cDNA clones of human BMI1, EZH2, MDM2, MDM4, and HIF1A were obtained from RIKEN BioResouce Center, Gene engineering division or National Institute of Technology and Evaluation.

The aforementioned cDNA fragments were inserted into lentivirus vectors (CSII-EF-RfAl, provided by Dr. Hiroyuki Miyoshi at RIKEN) by using LR clonase (Gibco-Invitrogen).

By means of lipofection (using Lipofectamine 2000, Invitrogen), the individual genes introduced into CSII-EF produced as described above, packaging constructs (pCAG-HIVgp, provided by Dr. Miyoshi), envelopes, and Rev constructs (pCMV-VSV-G-RSV-Rev, provided Dr. Miyoshi) were introduced into 293T cells serving as packaging cells (virus producing cells).

Three days after the gene introduction, the cell culture solution was recovered and passed through a 0.45-µm filter, and, subsequently, virus particles were precipitated and recovered by means of centrifugation (at 50,000 g for 2 hours). The recovered recombinant virus particles were suspended in a DMEM solution, subsequently dispensed in freezing tubes, and stored in a freezer (at −80° C.) until use.

Example 2: Creating Human Artificial Pluripotent Stem (iPS) Cells

A skin fragment was collected from a human abdomen and cultured in a cell culture plate by using a culture solution (DMEM/10% bovine serum). Because migration and proliferation of fibroblasts from the skin fragment were observed starting from the first week after culturing started, the fibroblasts were appropriately recovered and freeze-stored by using a trypsin/EDTA-containing phosphate-buffered saline solution (trypsin-EDTA).

The freeze-stored human fibroblasts were thawed, cultured again for several days, and, subsequently, gene introduction was performed in the culture plate by adding, at the same time, the lentivirus vectors that express OCT3/4, SOX2, KLF4, and c-MYC, which had been produced and freeze-stored as described above.

Four to six days after the gene introduction, infected cells were recovered by using trypsin-EDTA, and co-culturing thereof was started together with mouse-fetus-derived fibroblasts (feeder cells) prepared in advance, whose proliferation had been stopped by means of mitomycin C treatment. On the following day, the culture solution thereof was replaced with culture solution for human ES cells, and the culturing was continued.

Twenty to thirty days after the transduction of the genes for reprogramming factors by means of the lentivirus vectors, colonies showing an ES-cell-like morphology under microscopic observation were isolated as artificial pluripotent stem (iPS) cell clones by using microtips, and co-culturing thereof was performed together with separately prepared mouse-fetus-derived feeder cells. Subsequently, the culturing was continued while increasing the size of the culture vessel in accordance with cell proliferation.

Culturing to maintain the human iPS cells was performed in a polystyrene culture plate by using human-embryonic-stem cell culturing solution [DMEM-F12 (Wako Chemicals)/20% KSR (Gibco-Invitrogen)/bFGF (basic fibroblast growth factor, 10 ng/ml)/2-ME (2-mercaptoethanol, 50 µM with mitomycin C-treated mouse fetal fibroblasts] as feeder cells. Once in four to five days, depending on the cell proliferation, the cells were recovered by treating them for five to ten minutes with a CTK solution (collagenase-trypsin-KSR solution, according to Biochemical and Biophysical Research Communications 345: 926-932, 2006), and the culturing was continued by inoculating them into a culture vessel of an appropriate size.

Example 3: Differentiation Induction of Human Artificial Pluripotent Cells into Myeloid Blood Cells (iPS-MC)

(1) Preparation of OP9 Feeder Cells

Mouse-derived cultured cell line OP9 treated with mitomycin C (with 0.01 mg/ml for 60 min.) was inoculated into a gelatin-coated dish, and was used next day or later.

(2) Differentiation Induction Culturing

Undifferentiated iPS cells were treated for five to ten minutes using a CTK solution and recovered in a DMEM culturing solution containing fetal calf serum (FCS). The cells were suspended in α-MEM/20% FCS, and inoculated onto the OP9 feeder cells, thus starting differentiation induction culturing. Thereafter, the culturing was continued while exchanging the culture solution (α-MEM/20% FCS) once every three days.

Eighteen days after differentiation induction started, the cells were recovered by dissociating them by means of treatment using a trypsin-EDTA (ethylenediamine tetraacetic acid)-collagenase solution (at 37° C. for 60 min.), and a cell suspension was produced by means of pipetting. Then, the cells obtained from one dish having a diameter of 10 cm were suspended in 10 ml of DMEM/10% FCS, and inoculated onto two dishes having neither feeder cells nor gelatin coating. After two to five hours, cells that did not adhere to the dishes were recovered and passed through a 100-µm mesh (cell strainer, manufactured by BD Falcon), and thus, a cell suspension from which clumped cell aggregations had been removed was obtained.

The cells which passed through the mesh were allowed to float in α-MEM/20% FCS/human GM-CSF (100 ng/ml, manufactured by Peprotech)/human M-CSF (50 ng/ml, manufactured by Peprotech), and cultured without using OP9 feeder cells. Subsequently, it was observed that floating or weakly adherent cells appeared after the passage of about 3 to 9 days and that the number of the cells increased day by day. A photomicrograph of the differentiated cell derived from iPS cells is shown in FIG. 2.

The aforementioned floating cells were recovered, and inspected for expression of CD45, which is a leucocyte marker molecule, and expression of CD11b and CD33, which are myeloid cell marker. At first, the cells were treated with a Fc receptor blocking reagent (manufactured by Myltenyi Biotec) for ten minutes in order to inhibit non-specific binding of antibodies. Subsequently, the cells were stained with a fluorescein isothiocyanate (FITC)-labeled anti-human CD45 monoclonal antibody, phycoerythrin (PE)-labeled anti-human/mouse CD 11b antibodies, or a PE-labeled anti-human CD33 antibody at room temperature for forty minutes. Additionally, for negative controls, the cells were isotype-matched control antibodies labeled with identical fluorescent dyes.

Then, the cells were washed with PBS/2% FCS two times, the washed cells were analyzed by means of a flow cytometer (product name: "FACScan", manufactured by Becton Dickinson) equipped with a software "CellQuest".

The results obtained from inspection of molecules expressed on the surface of the cells are shown in FIG. 3. FIG. 3 shows Histograms in which the specific stained patterns and the staining patterns with isotype-matched control antibodies are merged together. Accoding to the results shown in the figure, it is understood that the floating cells, which had been obtained by the induction of differentiation of human iPS cells, express CD 45 which is a leucocyte marker molecule. Furthermore, it is understood that the number of the cells express CD11b or CD33 which is a maker molecule of myeloid blood cells. Said cells which were derived from iPS cells and which expressed the maker molecules of myeloid blood cells were designated as "iPS-MC" (iPS cell-derived myeloid cells).

Example 4: Imparting Long-Term Proliferative Capability to the iPS-MC by Introduction of cMYC and BMI1 (Preparation of iPS-ML)

The iPS-MC prepared in the previous section was cultured in a 24-well culture plate, and this was infected by adding thereto, separately or at the same time, suspensions of lentiviruses expressing cMYC or BMI1. From the day after the gene introduction, the culturing scale was expanded by adding a culture solution depending on cell proliferation. As the culture solution, α-MEM/20% FCS/human GM-CSF (100 ng/mL)/human M-CSF (50 ng/mL) was used continuously.

When infected only with the lentiviruses expressing cMYC, the iPS-MC proliferated at a rate of about 2-day doubling time. However, the proliferation stopped after about two-weeks from the lentivirus infection. As a result, with the forced expression of cMYC by the lentiviruses, the iPS-MC proliferated by a factor of about 30 to 100, and then, the proliferation stopped.

Even if the iPS-MC whose proliferation had stopped with the passage of two weeks or longer after being infected only with the cMYC lentiviruses was further infected with the cMYC lentiviruses, subsequent cell proliferation was not observed.

When infected only with the BMI1 lentiviruses, the iPS-MC proliferated slowly, and the proliferation thereof stopped after the number of cells increased about two- to three-fold.

When infected with the lentivirus expressing cMYC and that expressing BMI1 at the same time, the iPS-MC proliferated at a greater rate than when infected only with the cMYC lentivirus. In addition, unlike when infected only with the cMYC lentivirus, the proliferation continued even after the second week from the lentivirus infection. The iPS-MC that acquired the ability to proliferate for an extended period of time in this way was named iPS-ML (iPS-MC line, iPS cell-derived myeloid cell line, iPS cell-derived myeloid blood cell line possessing a long-term proliferative capability).

Culturing of the proliferating iPS-ML was continued while maintaining a constant cell concentration ($1 \times 10^5$ to $1 \times 10^6$ cells/mL). The iPS-ML continued to proliferate at a constant rate (doubling time of about 2-3 days) for four months after being infected with the lentiviruses. FIG. 4 shows a micrograph of the iPS-ML.

FIG. 5 shows results of the flow cytometer analysis, in which expression of CD45, Cd11b, and CD33 in the iPS-ML was inspected. From the results, it was confirmed that the iPS-ML expressed CD45 which is a leucocyte marker molecule, and CD11b and CD33 which are myeloid cell marker molecule, on the cell surface.

Example 5: Investigating Requirement of M-CSF and GM-CSF in the Proliferation of iPS-ML The iPS-ML continuously cultured for two months after being infected with the lentiviruses expressing cMYC and BMI1 was recovered, inoculated into a 96-well culture plate (FALSCON 353072) ($5 \times 10^3$ cells/well), and cultured. Then, proliferation rates were compared between the case in which the culture solution contained GM-CSF and M-CSF and the case in which the culture solution did not contain them.

Forty-eight hours after culturing was started in the 96-well culture plate, $^3$H-methyl-thymidine was added (37 Kbq/well), and, 18 hours thereafter, high-molecular-weight DNAs in the cells wre captured in a glass filter by using a cell harvester (Wallac). Then, incorporation of $^3$H-thymidine into the high-molecular-weight DNAs was measured by means of scintillation measurement (a MicroBeta system manufactured by Wallac was used). The incorporation of $^3$H-thymidine into the high-molecular-weight DNAs is proportional to the rate of DNA synthesis, that is to say, cell proliferation.

FIG. 6 shows the result of the scintillation measurement. From this result, it is understood that proliferation of iPS-ML requires about 50 ng/mL of M-CSF to be contained in the culturing solution. On the other hand, it is understood that GM-CSF is not necessarily required, but it has the effect of promoting proliferation.

Example 6: Analysis of Phagocytic Capacity of the iPS-ML on Fungal Particles (Zymosan) of Fungi Myeloid blood cells generally have strong phagocytic activity against microorganisms such as bacteria and fungi. Thus, the phagocytic activity of the iPS-ML against fungal particles (zymosan) of fungi was investigated. The iPS-ML in maintenance culturing was recovered from a culture flask by means of pipetting, and inoculated ($2 \times 10^5$ cells/well) into a 24-well culture plate (FALCON 353047) coated for cell culturing. The plate was left to stand for three hours, and FITC-labeled zymosan (Molecular Probe, Z2841) was added after confirming adherence of most of the iPS-ML to the bottom surface of the culture plate. After the passage of additional three hours, observation was performed using a fluorescence microscope.

FIG. 7 shows a micrograph thereof. The iPS-ML that adhered to the culture plate is seen in the bright-field image (captured with a phase-contrast Tense) on the left. The image on the right correspond to that obtained by capturing the same viewing field as that of the image on the left under conditions which detect fluorescence emitted by FITC. In this fluoroscopy image, it is confirmed that signals indicating localization of the FITC-labeled zymosan particles are concentrated as coinciding with the iPS-ML. This result showed that the iPS-ML phagocytosed the FITC-labeled zymosan particles.

Next, the progression over time of zymosan-particle phagocytosis by the iPS-ML was observed. The FITC-labeled zymosan was added to the iPS-ML that adhered to the 24-well culture plate, and the iPS-ML was recovered by using trypsin/EDTA after certain amounts of time (5, 10, 20, 40, and 80 min.) had passed. The proportion of cells having specific fluorescence, that is, cells that had phagocytosed the FITC-labeled zymosan, was analyzed by using the flow cytometer analyzer.

FIG. 8 shows a result obtained by the analysis with the flow cytometer. From this result, it was shown that the fraction of the iPS-ML that had phagocytosed the zymosan particles increased with the passage of time. In this experiment, about half of the iPS-ML had phagocytosed the zymosan particles during 30 minutes after adding the zymosan particles.

Example 7: Differentiation Induction of the iPS-ML into Dendritic-Cell-Like Cells (ML-DC)

Forty days after being simultaneously infected with the lentivirus expressing cMYC and the lentivirus expressing BMI1, the iPS-ML was cultured for four days in the presence of GM-CSF (100 ng/mL) and IL-4 (10 ng/mL) to induce differentiation thereof into the dendritic-cell-like cells (ML-DC). FIG. 9 shows the morphologies of the cells (in a phase-contrast micrograph) when cultured for additional two days by adding TNF (tumor necrosis factor)-α (10 ng/mL) thereto. It is recognized that cells having irregular morphologies with protrusions had formed clusters.

The ML-DC produced as described above was recovered by means of pipetting, and stained by using an anti-HLA Class II antibody, an anti-human 80 antibody, or an anti-human 86 antibody. Alternatively, the ML-DC was stained by using isotype-matched control antibodies labeled with FITC. Then, the cells were washed twice with PBS/2% FCS. The washed cells were analyzed by using the flow cytometer analyzer (product name "FACScan", manufactured by Becton Dickinson) equipped with CellQuest software.

FIG. 10 shows a result obtained by analysis with the flow cytometer after antibody staining. The figure shows specific staining patterns (solid line) overlaid on staining patterns in which the isotype-matched control antibodies were used (dotted line). From this analysis result, it was found that, in the same manner as physiologically occurring dendritic cells, the ML-DC expressed CD80, CD86, and HLA Class II, which relate to T-lymphocyte activation, on their cell surface.

Example 8: Investigation on T-Cell Stimulation Capability of the ML-DC

The ML-DC was prepared by culturing the iPS-ML for four days in the presence of GM-CSF (100 ng/mL) and IL-4 (10 ng/mL), and the cells were further cultured for additional two days by adding TNF (tumor necrosis factor)-α (10 ng/mL) thereto, and then, the cells were recovered. These cells were irradiated with X-rays at 45 Gy to stop the cell proliferation thereof, and then, said cells were inoculated into a 96-well round-bottom culture plate (FALCON 353077) (at $1 \times 10^2$ cells to $1 \times 10^4$ cells/well), and they were designated as stimulator cells. The ML-DC to which TNF-α had not been applied and the iPS-ML to which GM-CSF and IL-4 had not been applied were also irradiated with X-rays at 45 Gy to stop cell proliferation thereof, and then, said cells were inoculated into culture plates, and thus, they were also designated as stimulator cells. Then, donor-derived peripheral-blood allo-T cells were added thereto ($5 \times 10^4$ cells/well) as reactive cells, and they were cultured.

Four days after the culturing started, $^3$H-methyl-thymidine (37 Kbq/well) was added thereto. Eighteen hours thereafter, high-molecular-weight DNAs in the cells were captured on a glass filter by using a cell harvester (Wallac). The rate of the high-molecular-weight DNA synthesis, that is to say, the proliferation rate of the T cells, was quantified by measuring the radiation activity of $^3$H-thymidine captured on the glass filter by means of scintillation measurement (a MicroBeta system manufactured by Wallac was used).

FIG. 11 shows the result of the T-cell proliferation response analysis. It was found that the three types of stimulator cells (the iPS-ML, and the TNF-α-treated- or TNF-α-untreated-ML-DC) all possessed activity that stimulated allo-T cells and that induced their proliferation response. Also, it was understood that, of the three types of stimulator cells, the TNF-α-treated ML-DC possessed the strongest T-cell-stimulating capability. From the above results, it was shown that the ML-DC derived from the iPS-ML possessed powerful T-cell-stimulating capability.

Example 9: Preparation of iPS-ML by Introduction of cMYC and EZH2 into iPS-MC

The iPS-MC prepared in the above section was cultured in a 24-well culture plate, and suspensions of lentiviruses each expressing cMYC and EZH2 were added thereto at the same time to infect the cells, thereby preparing iPS-ML. FIG. 12 shows a micrograph of said cells. FIG. 13 shows results of investigation on expression of CD45, CD11b, CD33 and CD14 with a flow cytometer.

The iPS-ML obtained in this example proliferated at a much faster rate than the cells to which only cMYC was introduced. Furthermore, the resulting iPS-ML proliferated for a much longer time than the cells to which only cMYC was introduced, and thus, continued to proliferate at the second week or later after the infection of the lentiviruses.

Example 10: Preparation of iPS-ML by Introduction of cMYC and MDM2 into iPS-MC

The iPS-MC prepared in the above section was cultured in a 24-well culture plate, and suspensions of lentiviruses each expressing cMYC and MDM2 were added thereto at the same time to infect the cells, thereby preparing iPS-ML. FIG. 14 shows a micrograph of said cells. FIG. 15 shows results of investigation on expression of CD45, CD11b, and CD33 with a flow cytometer.

The iPS-ML obtained in this example proliferated at a much faster rate than the cells to which only cMYC was introduced. Furthermore, the resulting iPS-ML proliferated for a much longer time than the cells to which only cMYC was introduced, and thus, continued to proliferate at the second week or later after the infection of the lentiviruses.

Example 11: Preparation of iPS-ML by Introduction of cMYC and MDM4 into iPS-MC

The iPS-MC prepared in the above section was cultured in a 24-well culture plate, and suspensions of lentiviruses each expressing cMYC and MDM4 were added thereto at the same time to infect the cells, thereby preparing iPS-ML. FIG. 17 shows a micrograph of said cells. FIG. 15 shows results of investigation on expression of CD45, CD11b, and CD33 with a flow cytometer.

The iPS-ML obtained in this example proliferated at a much faster rate than the cells to which only cMYC was introduced. Furthermore, the resulting iPS-ML proliferated for a much longer time than the cells to which only cMYC was introduced, and thus, continued to proliferate at the second week or later after the infection of the lentiviruses.

Example 12: Preparation of iPS-ML by Introduction of cMYC and HIF1a into iPS-MC

The iPS-MC prepared in the above section was cultured in a 24-well culture plate, and suspensions of lentiviruses each expressing cMYC and HIF1a were added thereto at the same time to infect the cells, thereby preparing iPS-ML. FIG. 18 shows a micrograph of said cells. FIG. 19 shows results of investigation on expression of CD45, CD11b, and CD33 with a flow cytometer.

The iPS-ML obtained in this example proliferated at a much faster rate than the cells to which only cMYC was introduced. Furthermore, the resulting iPS-ML proliferated for a much longer time than the cells to which only cMYC was introduced, and thus, continued to proliferate at the second week or later after the infection of the lentiviruses.

Example 13: Induction of Differentiation of Human Artificial Pluripotent Stem Cells into Myeloid Blood Cells Without Use of Feeder Cells and Prepartaion of iPS-ML Undifferentiated human iPS cells were recovered by use of a CTK solution, and were cultured in a culture vessel coated with human fibronectin. That obtained by mixing OpTmizer™ T-Cell Expansion SFM (Life Technologies) and Stemline II Hematopoietic Stein Cell Expansion Medium (SIGMA) at 1:1, and Peprogro III (Peprotech) were sequentially used as the culture solution. Additionally, human BMP-4 (Bone Morphogenic Protein 4) was added to the culture solution at a concentration of 5 ng/mL to promote differentiation of the cells into mesodermal cells.

Twenty five days after culturing was started, the cells were treated with a trypsin-EDTA-collagenase solution (at 37° C., 60 minutes) to dissociate the cells therefrom, thereby recovering the same, and a cell suspension was prepared by pipetting. Then, the cells, which were derived from one dish having a diameter of 10 cm, were suspended in 10 mL of DMEM/10% FCS, and this was inoculated into two dishes of a diameter of 10 cm without feeder cells and without a gelatin coat. Two to five hours later, the cells which did not adhere to the dishes were recovered, and were passed through a 100-micron mesh (cell strainer manufactured by BD Falcon), thereby obtaining a cell suspension from which aggregated cell clumps were removed. Then, the cells were cryopreserved by use of a cell preservative solution ("Cell Banker" manufactured by JuJi Field, Inc.).

The cells which had been cryopreserved as described above were thawed, and cultured for ten days by use of α-MEM/20% FCS containing GM-CSF (50 ng/mL) and M-CSF (50 ng/mL). Consequently, it was observed that floating cells and adherent cells emerged and that they proliferated. FIG. 20 shows a micrograph of the cells. FIG. 21 shows results of investigation on expression of CD45, CD11b, and CD33 with a flow cytometer. From the results, it was confirmed that CD45, which is a leucocyte marker molecule, and CD11b and CD33, which are maker molecules of myeloid blood cells, were expressed on the cell surface. Accordingly, it was understood that said differentiated cells derived from the iPS cells are iPS-MC.

Next, the iPS-MC was recovered, and cultured in a 24-well culture plate. Suspensions of lentiviruses each expressing cMYC and BMI1 were added thereto at the same time to infect the cells, thereby preparing iPS-ML. FIG. 22 shows a micrograph of the cells. FIG. 23 shows results of investigation on expression of CD45, CD11b, and CD33 with a flow cytometer.

The iPS-ML obtained in this example proliferated at a much faster rate than the cells to which only cMYC was introduced. Furthermore, the resulting iPS-ML proliferated for a much longer time than the cells to which only cMYC was introduced, and thus, continued to proliferate at the second week or later after the infection of the lentiviruses.

Example 14: Imparting Long-Term Proliferative Capability to Human Peripheral Monocytes by Introduction of cMYC and BMI1

50 mL of peripheral blood was collected from a healthy donor by using a 50 mL injection syringe to which a small amount (about 0.5 mL) of heparin had been aspired. The blood was dispensed into two 50 mL centrifuge tubes at 25 mL each, and these were diluted with the equal amount of phosphate buffered saline (PBS). Then, the diluted blood of 25 mL was each slowly layered on 15 mL of a ficoll solution (GE Healthcare, 17-1440-03) which had been dispensed into a centrifuge tube (BD Falcon, 352070, etc.) in advance. Then, these were centrifuged for twenty minutes at a centrifugal force of 500 g by use of a centrifugal apparatus, and then, a fraction of mononuclear cells (a cell population containing lymphocytes and monocytes) which was present around the boundary face was recovered.

The recovered fraction of mononuclear cells was washed with a RPMI-1640 culture solution, and then, they were suspended in a buffer solution for separation with magnetic beads (PBS containing 2 mM of EDTA and 2% FCS). Then, anti-human CD14 antibody-bound magnetic micro-beads (manufactured by Miltenyi Biotec K.K., 130-042-201) were added thereto, and this was allowed to stand at 6° C. for fifteen minutes. Subsequently, this was washed with the buffer solution for separation with magnetic beads, and then, cells expressing CD14 on the cell surface, namely monocytes, were separated with a column for cell separation (MS column manufactured by Miltenyi Biotec K.K., 130-042-201). Additionally, commercially-available human peripheral monocytes for research use (Lonza, 2W-400C), which were separated in the same manner, were also used.

The human peripheral monocytes (CD14-positive cells) obtained in the above section were cultured in a 24-well culture plate, and a suspension of a lentivirus expressing cMYC and a suspension of a lentivirus expression BMI1 were added thereto at the same time, whereby the cells were infected. α-MEM/20% FCS/human GM-CSF (100 ng/mL)/human M-CSF (50 ng/mL) was used as the culture solution.

Until the second week after infection of the lentiviruses, any clear cell proliferation was not recognized. Since proliferation was confirmed in the third week or later, a culture solution was further added thereto, depending on the cell proliferation, and the culture scale was expanded. FIG. 24 shows a micrograph of cells about forty days after infection of the lentiviruses. In addition, FIG. 25 shows results of investigation on expression of CD45, CD11b, CD33 and CD14 with a flow cytometer with respect to the cells collected at the same period. From the results, it was confirmed that the monocyte-derived cells which acquired long-term proliferative capability due to the introduction of cMYC and BMI1 expressed myeloid blood cell markers. Consequently, the cells were named as Mo-ML (Monocyte-derived myeloid blood cell line).

Example 15: Induction of Differentiation of Mo-ML into Dendritic-Cell-Like Cells (ML-DC)

Forty days after being simultaneously infected with the lentiviruses each expressing cMYC and BMI1, the Mo-ML was cultured for four days in the presence of GM-CSF (100 ng/mL) and IL-4 (10 ng/mL) to induce differentiation thereof into the dendritic-cell-like cells (ML-DC). This was further cultured by adding TNF-α (10 ng/mL) thereto.

Investigation of expression of maker molecules on the cell surface of ML-DC was carried out by flow cytometry.

At first, the cells were treated with a Fc receptor blocking reagent (manufactured by Myltenyi Biotec). Subsequently, the cells were stained with a FITC-labeled anti-human 80 antibody, an anti-human 86 antibody, or an anti-HLA class II antibody at room temperature for forty minutes. Additionally, the cells were isotype-matched control antibodies labeled with FITC or PE. The stained cells were analyzed with FACScan (BD corporation).

The results obtained from the analysis with the flow cytometer after antibody staining are shown in FIG. 26. In this figure, specific staining patterns (solid line) are overlaid on staining patterns in which the isotype-matched control antibodies were used (dotted line). Form the analysis results, it was revealed that ML-DC expressed CD80, CD86 and HLA class II, which relate to activation of T lymphocytes, on the cell surface in the sama manner as physiologically-occurring dendritic cells.

Example 16: Inspection on T-Cell-Stimulating Capability of ML-DC Derived from Mo-ML The ML-DC was prepared by culturing the Mo-ML for four days in the presence of GM-CSF (100 ng/mL) and IL-4 (10 ng/mL), and the cells were further cultured for additional two days by adding TN-α (10 ng/mL) thereto, and then, the cells were recovered. These cells were irradiated with X-rays at 45 Gy to stop the cell proliferation thereof, and then, said cells were inoculated into a 96-well round-bottom culture plate (FALCON 353077) (at $1 \times 10^2$ cells to $1 \times 10^4$ cells/well), and they were designated as stimulator cells. The ML-DC to which TNF-α had not been applied and the Mo-ML to which GM-CSF and IL-4 had not been applied were also irradiated with X-rays at 45 Gy in the same way to stop cell proliferation thereof, and then, said cells were inoculated into culture plates, and thus, they were also designated as stimulator cells. Then, donor-derived peripheral-blood allo-T cells were added thereto (5×10$^4$ cells/well) as reactive cells, and they were cultured.

Four days after the culturing started, $^3$H-methyl-thymidine (37 Kbq/well) was added thereto. Eighteen hours later, high-molecular-weight DNAs in the cells were captured on a glass filter by using a cell harvester (Wallac). The radiation activity of $^3$H-thymidine captured on the glass filter was determined by means of scintillation measurement to quantify a proliferation rate of the T cells.

FIG. 27 shows the result of the T-cell proliferation response analysis. It was found that the three types of stimulator cells (the iPS-ML, and the TNF-α-treated- or TNF-α-untreated-ML-DC) all possessed activity that stimulated allo-T cells and that induced their proliferation response. Also, it was understood that, of the three types of stimulator cells, the TNF-α-treated ML-DC possessed the strongest T-cell-stimulating capability. From the above results, it was shown that the ML-DC derived from the Mo-ML possessed powerful T-cell-stimulating capability.

Example 17: Preparation of Mo-ML by Introduction of cMYC and MDM2 into Peripheral Monocytes Human peripheral monocytes (CD14-positive cells) were cultured in a 24-well culture plate, and suspensions of lentiviruses each expressing cMYC and MDM2 were added thereto at the same time to infect the cells. α-MEM/20% FCS/human GM-CSF (100 ng/mL)/human M-CSF (50 ng/mL) was used as the culture solution. The cells exhibited clear proliferation tendency in the third week or later after the lentiviruses were infected. FIG. 28 shows a micrograph of cells about one month after infection of the lentiviruses. FIG. 29 shows results of investigation on expression of CD45, CD11b, CD33 and CD14 at the same period.

Example 18: Preparation of Mo-ML by Introduction of cMYC, EZH2 and MDM2 into Peripheral Monocytes Human peripheral monocytes were cultured in a 24-well culture plate, and suspensions of lentiviruses each expressing cMYC, EZH2 and MDM2 were added thereto at the same time to infect the cells. The cells exhibited clear proliferation tendency in the third week or later after the lentiviruses were infected. FIG. 30 shows a micrograph of cells about one month after infection of the lentiviruses. FIG. 31 shows results of investigation on expression of CD45, CD11b, CD33 and CD14 at the same period.

The invention claimed is:

1. An in vitro method of producing a human myeloid blood cell, comprising forcedly expressing
    (A) an exogenous cMYC gene, and
    (B) at least one exogenous gene selected from the group consisting of an EZH2 gene, an MDM2 gene, an MDM4 gene, and an HIF1A gene
    in a human myeloid blood cell by introducing the exogenous cMYC gene and the at least one gene selected from the group consisting of an EZH2 gene, an MDM2 gene, an MDM4 gene, and an HIF1A gene into said human myeloid blood cell which was derived from human iPS cells, to form a human myeloid blood cell which can proliferate for two weeks or more from the time point when the exogenous genes are forcedly expressed.

2. The method according to claim 1, wherein the cMYC gene, the EZH2 gene, the MDM2 gene, the MDM4 gene and the HIF1A gene are a human cMYC gene, a human EZH2 gene, a human MDM2 gene, a human MDM4 gene and a human HIF1A gene, respectively.

3. A method of producing a human myeloid blood cell possessing a proliferative capability, comprising:
    providing a human myeloid blood cell derived from human iPS cells; and
    introducing an exogenous cMYC gene and at least one exogenous gene selected from the group consisting of an EZH2 gene, an MDM2 gene, an MDM4 gene, and an HIF1A gene into said human myeloid blood cell to form a human myeloid blood cell which expresses the introduced exogenous genes and which can proliferate for two weeks or more from the time point when the exogenous genes are expressed.

4. A method of producing a human myeloid blood cell line possessing a proliferative capability, comprising:
    providing a human myeloid blood cell derived from human iPS cells; and
    introducing an exogenous cMYC gene and an exogenous BMI1 gene into said human myeloid blood cell to form a human myeloid blood cell line which expresses the introduced exogenous genes and which can proliferate for two weeks or more from the time point when the exogenous genes are expressed.

5. A method of producing a human myeloid blood cell line possessing a proliferative capability, comprising:
    providing a human myeloid blood cell derived from human iPS cells; and
    introducing an exogenous cMYC gene, an exogenous BMI1 gene, and an exogenous MDM2 gene into said human myeloid blood cell to form a human myeloid blood cell line which expresses the introduced exogenous genes and which can proliferate for two weeks or more from the time point when the exogenous genes are expressed.

* * * * *